United States Patent [19]
Hester, Jr. et al.

[11] 3,933,794
[45] Jan. 20, 1976

[54] 2-(2-ALKYNYLAMINO)-3H-1,4-BENZODIAZEPINES

[75] Inventors: Jackson B. Hester, Jr., Galesburg, Mich.; Arthur R. Hanze, deceased, late of Kalamazoo, Mich., by Janice W. Hanze, administratrix

[73] Assignee: The Upjohn Company, Kalamazoo, Mich.

[22] Filed: Sept. 10, 1973

[21] Appl. No.: 395,510

Related U.S. Application Data

[62] Division of Ser. No. 169,091, Aug. 4, 1971, abandoned.

[52] U.S. Cl. ............ 260/239 BD; 260/332.2 R; 260/332.3 P; 260/332.5; 260/347.2; 260/347.3; 260/347.7; 424/244; 424/263; 424/269; 260/239.3 D; 260/256.4 R; 260/256.5 R; 260/294.8 C; 260/295 T; 260/295 K; 260/295 F; 260/296 B; 260/309; 260/326.34; 260/326.5 CA; 260/326.9; 260/329 S; 260/329 F
[51] Int. Cl.²............ C07D 243/20; C07D 401/04
[58] Field of Search.... 260/239 BD, 296 B, 294.8 C

[56] References Cited
UNITED STATES PATENTS

| | | |
|---|---|---|
| 2,893,992 | 7/1959 | Sternbach et al. ........... 260/239 BD |
| 3,320,239 | 5/1967 | Stempel et al. .............. 260/239 BD |
| 3,422,091 | 1/1969 | Archer et al. ............... 260/239 BD |

OTHER PUBLICATIONS

Sternbach et al., Psychopharmacological Agents, M. Gordon, ed., Vol. I, (Academic Press, 1964), p. 145.

*Primary Examiner*—Alton D. Rollins
*Attorney, Agent, or Firm*—John T. Reynolds; Ward F. Nixon

[57] ABSTRACT

Novel 6-substituted 4H-imidazo[1,2-a][1,4]benzodiazepines, the intermediate 5-substituted-2-(2-alkynylamino)-3H-1,4-benzodiazepines, pharmacologically acceptable acid addition salts thereof, and processes for their production. The compounds of this invention and the pharmacologically acceptable acid addition salts thereof are central nervous system depressants. They are useful as sedatives, hypnotics, tranquilizers, muscle relaxants and anticonvulsants, and also as feed additives for increasing growth rate and feed efficiency of livestock and poultry, milk production in the mammalian species and egg production in avian species.

3 Claims, No Drawings

2-(2-ALKYNYLAMINO)-3H-1,4-BENZODIAZEPINES

This is a division of application Ser. No. 169091, filed Aug. 4, 1971, now abandoned.

SUMMARY OF THE INVENTION

The novel 6-substituted 4H-imidazo[1,2-a][1,4]benzodiazepines of this invention are illustratively represented by generic formulae, I, II and III, and the novel intermediate 5-substituted-2-(2-alkynylamino)-3H-1,4-benzodiazepines by generic formula IV as follows:

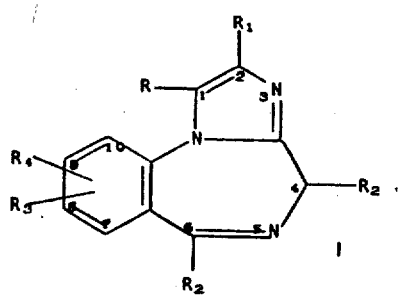

I

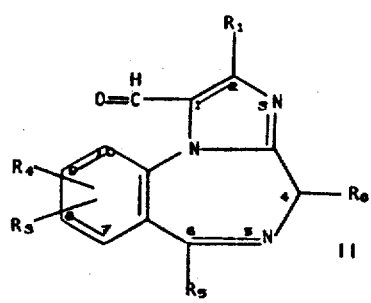

II

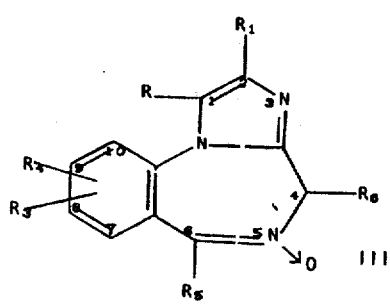

III

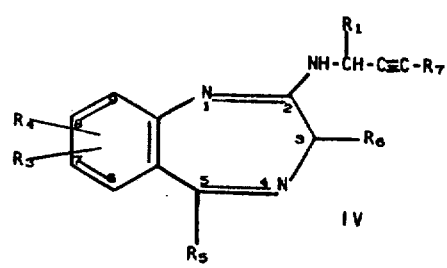

IV wherein R is selected from the group consisting of hydrogen, methyl, ethyl and propyl; $R_1$ and $R_6$ are each selected from the group consisting of hydrogen and alkyl of 1 to 3 carbon atoms, inclusive; $R_2$ is selected from the group consisting of hydrogen, alkyl of 1 to 3 carbon atoms, inclusive, hydroxy, acetoxy and propionoxy; $R_3$ and $R_4$ are each selected from the group consisting of hydrogen, alkyl of 1 to 3 carbon atoms, inclusive, halogen, nitro, cyano, amino, trifluoromethyl, alkoxy, alkylthio, alkylsulfinyl, alkylsulfonyl, alkanoylamino and dialkylamino in which the carbon chain moieties are of 1 to 3 carbon atoms, inclusive; $R_5$ is selected from the group consisting of pyridyl, 2-pyrimidyl, furyl, pyrryl, thienyl, alkyl of 1 to 3 carbon atoms, inclusive, alkenyl of 2 to 3 carbon atoms, inclusive, cycloalkyl of 5 to 7 carbon atoms, inclusive, cycloalkenyl of 5 to 7 carbon atoms, inclusive, and a phenyl radical of the formula

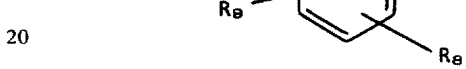

in which $R_8$ and $R_9$ each have the same meanings as given above for $R_3$ and $R_4$; and $R_7$ is selected from the group consisting of hydrogen, methyl and ethyl.

In this application the term alkyl is exemplified by methyl, ethyl, propyl and isopropyl. The term halogen is exemplified by fluoro, chloro, and bromo. The term alkoxy is exemplified by methoxy, ethoxy, propoxy and isopropoxy. The term alkylthio is exemplified by methylthio, ethylthio, propylthio and isopropylthio. The term alkylsulfinyl is exemplified by methylsulfinyl, ethylsulfinyl, propylsulfinyl and isopropylsulfinyl. The term alkylsulfonyl is exemplified by methylsulfonyl, ethylsulfonyl, propylsulfonyl and isopropylsulfonyl. The term alkanoylamino is exemplified by formylamino, acetylamino, propionylamino and isopropionylamino. The term dialkylamino is exemplified by dimethylamino, diethylamino, methylethylamino, methylpropylamino, ethylpropylamino, dipropylamino, diisopropylamino and the like. The term alkenyl is exemplified by vinyl, 1-propenyl, allyl and isopropenyl. The term cycloalkyl is exemplified by cyclopentyl, cyclohexyl and cycloheptyl. The term cycloalkenyl is exemplified by 1-cyclopentenyl, 1-cyclohexenyl, 1-cycloheptenyl, 2-cyclopentenyl, 2-cyclohexenyl, 2-cycloheptenyl 4-cycloheptenyl.

The novel 6-substituted 4H-imidazo[1,2-a][1,4]benzodiazepines of formulae I, II and III, above, and the intermediate 5-substituted (2-(2-alkynylamino)-3H-1,4-benzodiazepines of formula IV exist in either the non-protonated (free base) form or in the protonated (acid addition salt) form, depending on the pH of the environment. They form stable protonates, i.e., pharmacologically acceptable acid addition salts, on acidification of the free base with suitable pharmacologically acceptable acids, for example, hydrochloric, hydrobromic, sulfuric, phosphoric, nitric, acetic, propionic, palmitic, benzoic, salicylic, hexynoic, phenylbutyric, naphthoic, glycolic, succinic, nicotinic, tartaric, maleic, malic, pamoic, methanesulfonic, cyclohexanesulfonic, citric, and lactic acids, and the like. Conversely, the free bases of the novel compounds of formulae I, II, III and IV can be obtained from a salt, (e.g., from the hydrochloride or sulfate salt) by neutralization with a base such as sodium hydroxide, extracting with an immiscible solvent, for example chloroform, drying the extract, for example with anhydrous sodium sulfate, and removing the solvent by evaporation.

The novel compounds of formulae I, II and III and the pharmacologically acceptable acid addition salts thereof have sedative, hypnotic, anticonvulsant, tranquilizing and muscle relaxant effects in mammals and birds, and as feed additives for increasing the growth rate and feed efficiency of livestock and poultry, milk production during lactation in the mammalian species and egg production in the avian species.

Sedative effects of the compounds of this invention are shown by the following tests in mice:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves a standard pedestal in less than a minute to climb back to the floor of the standard mouse box. Tranquilized mice will stay on the pedestal for more than 1 minutes.

Nicotine antagonism test: Mice in a group of 6 are injected with the text compound. Thirty minutes later the mice including control (untreated) mice are injected with nicotine salicylate (2 mg./kg.). The control mice show over-stimulation, i.e., (1) running convulsions followed by (2) tonic extensor filts; followed by (3) death.

Antagonism to strychnine (as sulfate): The test consists in orally administering into groups of 6 mice the test compound, and 30 minutes later 3 mg./kg. strychnine sulfate intraperitoneally. The survivors after 4 hours reflect the activity of the compound as a muscle relaxant and antispasmodic. A dosage of 3 mg./kg. of strychnine sulfate is routinely fatal to all the control mice.

The following compounds typical of this invention have (by intraperitoneal injection) $ED_{50}$ as shown in the table below.

| COMPOUND | $ED_{50}$ (in mg./kg.) | | | | |
|---|---|---|---|---|---|
| | Ch | D | P | Ni | Str |
| 8-chloro-1-methyl-6-phenyl-4H-imidazo[1,2-a]-[1,4]benzodiazepine | 25.0 | 5.0 | 28.0 | 1.8 | 79.0 |
| 8-chloro-6-(2-chloro-phenyl)-1-methyl-4H-imidazo[1,2-a][1,4]benzo-diazepine | 0.5 | 0.23 | 0.4 | 0.13 | 1.8 |
| 8-chloro-6-phenyl-4H-imidazo[1,2-a][1,4]benzo-diazepine 1-carboxaldehyde | 4.0 | 0.8 | 2.8 | 0.36 | 11.0 |

Ch = chimney test
D = dish test
P = pedestal test
Ni = nicotine antagonism (3) test
Str = strychnine antagonism The pharmaceutical forms contemplated by this invention include pharmaceutical compositions suited for oral, parenteral and rectal use, e.g., tablets, powder packets, chachets, dragees, capsules, solutions, suspensions, sterile injectable forms, suppositories, bougies, and the like. Suitable diluents or carriers such as carbohydrates (lactose, proteins, lipids, calcium phosphate, cornstarch, stearic acid, methylcellulose and the like can be used as carriers or for coating purposes. Oil, e.g., coconut oil, sesame oil, safflower oil, cottonseed oil, peanut oil can be used for preparing solutions or suspensions of the active drug. Sweetening, coloring, and flavoring agents can be added.

For mammals and birds, food premixes, with starch, oatmeal, dried fishmeat, fishmeal, flour and the like can be prepared. These are then incorporated into an animal feed.

As feed additives the compounds of formulae I, II and III can be used in dosages of 0.003 mg. to 50 mg./animal/day in a feed to increase growth, feed consumption and feed efficiency in livestock and poultry, milk production in the mammalian species and egg production in avian species.

As transquilizers the compounds of Formulae I, II and III can be used in dosages of 0.01 mg. to 20.0 mg./kg. in oral or injectable preparations as described above, to alleviate tension and anxiety in mammals, or birds, such as e.g., occurs when animals are traveling.

The novel compounds of this invention and processes for their production are illustratively represented by the following sequence of formulae:

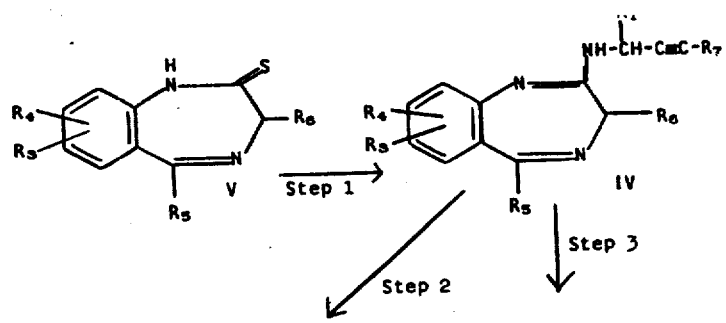

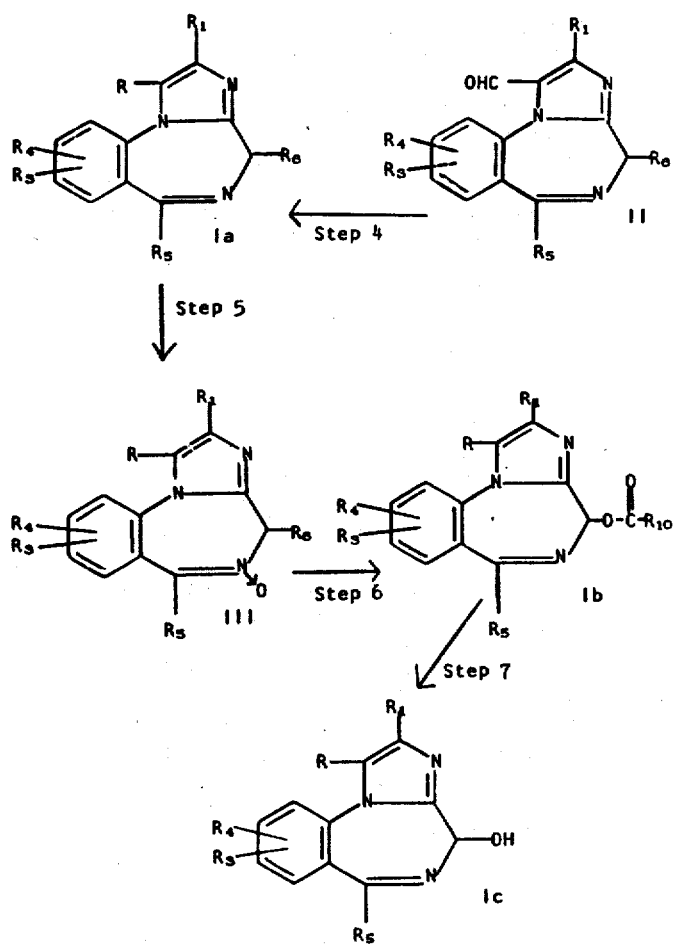

wherein R, $R_1$, $R_3$, $R_4$, $R_5$, $R_6$ and $R_7$ have the meanings previously given and $R_{10}$ is selected from the group consisting of methyl and ethyl.

The compounds of formula 1a, 1b and 1c are combined above to form the compounds of generic formula 1.

The starting materials of formula V are prepared by heating a known corresponding compound of the formula:

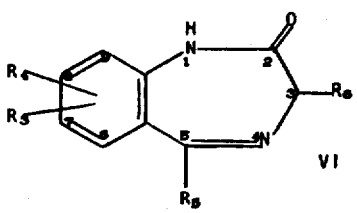

wherein $R_3$, $R_4$, $R_5$ and $R_6$ have the same meanings as previously given, with phosphorus pertasulfide in a solvent such as pyridine, benzene, toluene or xylene at between about 80° to about 140° C. for between about 30 minutes to about 6 hours in accordance with the procedure disclosed by Archer et al., J. Org. Chem. 29, 231 (1964) and U.S. Pat. No. 3,422,091. The preparation of compounds of Formula VI are described in U.S. Pat. Nos. 3,100,770; 3,179,656; 3,268,586; 3,338,886; 3,466,328; 3,422,091 and 3,573,282; Belgian Pat. Nos. 619,101 and 662,240; French Pat. Nos. 1,391,752 and 1,455,048; Netherlands Pat. Nos. 65/07637; and 69/08966; J. Pharm. Sci. 53, 264; and Earley et al., J. Med. Chem. 11, 774 (1968).

The process of this invention comprises the following steps:

1. A 1,3-dihydro-2H-1,4-benzodiazepine-2-thione (V) in a solvent such as benzene, tetrahydrofuran, dioxane, ethylene-glycol dimethylether and the like, is reacted with the appropriate 2-alkynylamine of the formula:

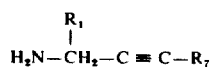

wherein $R_1$ and $R_7$ have the meanings previously given to obtain the corresponding 2-(2-alkynylamino)-3H-1,4-benzodiazepine (IV). The following are examples of 2-alkynylamines which can be used.

2-propynylamine (propargyl amine),
1-methyl-2-propynylamine,
1-ethyl-2-propynylamine,
1-propyl-2-propynylamine,
1-isopropyl-2-propynylamine, 2-butynylamine,
1-methyl-2-butynylamine,
1-ethyl-2-butynylamine,
1-propyl-2-butynylamine,
1-isopropynyl-2-butynylamine,
2-pentynylamine,
1-methyl-2-pentynylamine,
1-ethyl-2-pentynylamine,
1-propyl-2-pentynylamine, and
1-isopropyl-2-pentynylamine.

The reaction is preferably carried out within a temperature range of from about 25° C. to about 50° C. for a period of from about 2 to 10 hours. The product IV thus obtained is recovered from the reaction mixture by conventional methods, for example the solvent is removed by distillation and the residue thus obtained is crystallized from a suitable solvent such as, an alkanol, e.g., methanol, ethanol, propanol, isopropanol and the like, methylene chloride, ethyl acetate, mixtures thereof and the like to obtain the desired compound IV.

2. The 2-(2-alkynylamino)-3H-1,4-benzodiazepines (IV) thus obtained are treated with a mercuric salt in the presence of an aqueous mineral acid solution, at a temperature within the range of from about 10° C. to about 50° C. for a period of from about 1 to 24 hours to obtain the corresponding 4H-imidazo[1,2-a][1,4]benzodiazepines of formula 1a, wherein R is methyl, ethyl or propyl. Mineral acids which can be used are, for example, phosphoric, hydrochloric and sulfuric acids. Mercuric salts which can be used are for example mercuric sulfate, mercuric chloride, mercuric phosphate, mercuric fluoride, mercuric acetate and the like. Wherever possible it is desirable to use an acid or a salt having the same anion, of these sulfuric acid and mercuric sulfate are preferred. In carrying out the reaction, it is advantageous to use about a 50% aqueous solution of sulfuric acid. The compounds of formula Ia a thus obtained are recovered from the reaction mixture and purified by conventional methods, for example by chromatography on silica gel and crystallization from a suitable organic solvent such as benzene, toluene, chloroform, methylene chloride, ethyl acetate, hexanes, mixtures thereof and the like.

3. The 2-(2-propynylamino)-3H-1,4-benzodiazepines of formula IV, i.e., those compounds where $R_7$ is hydrogen are converted to the corresponding 4H-imidazo[1,2-a][1,4]benzodiazepine 1-carboxaldehydes of formula II, by treating the selected compound IV with mercuric acetate in an aqueous acetic acid-formic acid medium at a temperature within the range of from about 20° C. to about 50° C. for a period of from about 1 to 10 hours. The compounds of formula II are recovered from the reaction mixture and purified by conventional methods, for example chromatography and crystallization as described in Step 2, above.

4. The 1-carboxaldehydes of formula II are converted to the corresponding compounds of formula Ia, wherein R is hydrogen by treating the selected compound II in a suitable organic solvent such as benzene, toluene, tetrahydrofuran, methylene chloride and the like, with tris(triphenylphosphine)rhodium chloride at reflux temperature for a period of from about 1 to 12 hours. The product (Ia) thus obtained is recovered and purified by conventional methods, for example in the manner described in Step 2, above.

5. The 5-oxides of formula III are obtained by reacting a compound of formula Ia with a peracid, such as peracetic acid, perphthalic acid, perbenzoic acid, m-chloroperbenzoic acid and the like, in a suitable organic solvent such as a lower alkanol, e.g., methanol ethanol, propanol, isopropanol and butanol; chloroform, methylene chloride and the like at a temperature within the range of from about 0° C. to about 25° C. for a period of from about 6 to 48 hours. The 5-oxides are recovered from the reaction medium and purified by conventional methods such as chromatography and/or crystallization.

6. The 5-oxides of formula III thus obtained, wherein $R_6$ is hydrogen, are then converted to the corresponding 4-acetates and propionates by reacting the selected 5-oxide with acetic anhydride or propionic anhydride or with a mixture of the anhydride and the corresponding acid at a temperature of from about 100° C. to about 140° C. for a period of from about 10 minutes to about 1 hour. The 4-acetate or 4-propionate thus obtained, is recovered from the reaction mixture and purified by conventional methods such as chromatography and/or crystallization from a suitable solvent as described in Step 2, above.

7. The 4-acetates and 4-propionates of formula Ib are hydrolyzed to the corresponding free alcohols of formula Ic in accordance with methods known in the art, for example the selected acylate (1b) is treated with a dilute aqueous solution of an alkali metal hydroxide, e.g., sodium or potassium hydroxide, at low temperature preferably within the range of about −10° C. to about +10° C. for a period of from about 1 to 5 hours. The free alcohol Ic, thus obtained, is recovered from the reaction medium and purified by conventional methods such as chromatography and/or crystallization. For example in the manner described in Step 2, above.

The following Preparations and Examples are illustrative of the products and processes of the present invention but are not to be construed as limiting.

PREPARATION 1

1,3-Dihydro-7-chloro-5-(2,6-difluorophenyl)-2H-1,4-benzodiazepin-2-one (VI)

A. 2-Acetamido-5-chloro-2',6'-difluorobenzophenone

To a solution of 114 g. (1.0 mole) of m-difluorobenzene in 800 ml. of dry tetrahydrofuran cooled to −50° C. and maintained under a nitrogen atmosphere is added, with stirring, 320 ml. of an n-heptane solution of n-butyl lithium containing 1.0 mole of the latter. The addition is carried out during 50 minutes and is followed by stirring 2 hours more at −50° C. The cold solution is then added with stirring during 50 minutes to a solution of 187.8 g. (0.97 mole) of 6-chloro-2-methyl-4H-3,1-benzoxazin-4-one [J. Am. Chem. Soc. 70, 2423 (1948)] in 1400 ml. of benzene and 1000 ml. of tetrahydrofuran at 25° C. The mixture is stirred under a nitrogen atmosphere for 20 hours, at which time 1000 ml. of 2N hydrochloric acid is added. The aqueous layer is separated and discarded. The organic layer is filtered to remove suspended solid material and the filtrate is washed with cold, dilute aqueous sodium hydroxide solution. Three layers are present, a light colored aqueous phase, a dark brown aqueous phase, and an organic phase. The organic phase, after being dried with anhydrous sodium sulfate, is concentrated to give 101 g. of a semi-solid which is then extracted with 2100 ml. of hot Skellysolve B hexanes. Evaporation of the extract gives 39.9 g. of crude product, m.p.

106°–116° C. Recrystallization of this material from Skellysolve B gives purified 2-acetamido-5-chloro-2',-6'-difluorobenzophenone, m.p. 118°–120° c.

Anal. Calcd. for $C_{15}H_{10}ClF_2NO_2$: C, 58.17; H, 3.25; Cl, 11.45; P, 12.27; N, 4.52. Found: C, 58.11; H, 3.38; Cl, 11.53; P, 12.24; N, 4.20.

B. 2-Amino-5-chloro-2', 6'-difluorobenzophenone

A suspension of 4.2 g. (0.014 mole) of 2-acetamido-5-chloro-2',6'-difluorobenzophenone in 350 ml. of concentrated hydrochloric acid and 350 ml. of water is heated on a steam bath with stirring and in a nitrogen atmosphere until complete solution results. The solution is cooled and made basic with 50% aqueous sodium hydroxide solution. The resulting solid is removed by extraction with methylene chloride. The extract is dried with anhydrous sodium sulfate and evaporated to dryness. The residue thus obtained is recrystallized from cyclohexane to give 2.4 g. of 2-amino-5-chloro-2',6'-difluorobenzophenone, m.p. 103°–105° C.

Anal. Calcd. for $C_{13}H_{10}ClF_2NO$: C, 58.33; H, 3.01; Cl, 13.24; F, 14.20; N, 5.23. Found: C, 58.33; H, 3.29; Cl, 13.31; F, 14.87; N, 5.14.

C.
2-(2-Bromoacetamido)-5-chloro-2',6'-difluorobenzophenone

To a solution of 2.7 g. (0.01 mole) of 2-amino-5-chloro-2',6'-difluorobenzophenone To a solution of 2.7 g. (0.01 mole) of 2-amino-5-chloro-2',6'-difluoro-benzophenone in 100 ml. of benzene, through which a rapid stream of nitrogen is passed, is added 3.03 g. (0.015 mole) of bromoacetyl bromide. A precipitate is formed soon after the addition is complete. The benzene is removed by evaporation and the solid residue thus obtained is recrystallized from cyclohexane to yield 3.4 g. of 2-(2-bromoacetamido)-5-chloro-2',6'-difluorobenzophenone, m.p. 146°–147.5° c.

Anal. Calcd. for $C_{15}H_9BrClF_2NO_2$: C, 46.36; H, 2.33; Br, 20.56; Cl, 9.12; F, 9.78; N, 3.60. Found: C, 46.46; H, 2.48; Br, 20.68; Cl, 9.21; F, 9.49; N, 3.82.

D.
2-(2-Aminoacetamido)-5-chloro-2',6'-difluorobenzophenone

Liquid ammonia (350 ml.) is added to a solution of 26 g. (0.067 mole) of 2-(2-bromoacetamido)-5-chloro-2',6'-difluorobenzophenone in 350 ml. of methylene chloride. The solution is stirred under reflux for 5 hours and is then stirred for about 16 hours while excess ammonia is evaporated. The methylene chloride solution is filtered to remove solid material and the filtrate is then evaporated to dryness. The residue thus obtained is recrystallized from 2 l. of cyclohexane to give 19.4 g. of 2-(2-aminoacetamido)-5-chloro-2',6'-difluorobenzophenone, m.p. 133°–135° C.

Anal. Calcd. for $C_{15}H_{11}ClF_2N_2O_2$: C, 55.48; H, 3.42; Cl, 10.92; F, 11.70; N, 8.63. Found: C, 56.69; H, 3.99; Cl, 11.19; F, 11.06; N, 8.34.

E.
1,3-Dihydro-7-chloro-5-(2,6-difluorophenyl)-2H-1,4-benzodiazepin-2-one A solution of 21.0 g. (0.065 mole) of 2-(2-aminoacetamino)-5-chloro-2',6'-difluorobenzophenone in 300 ml. of pyridine is heated under reflux in a nitrogen atmosphere for 18 hours. The pyridine is removed by evaporation. The residue after being washed with Skellysolve B hexanes is recrystallized, first from ethyl acetate-Skellysolve B hexanes and then from ethyl acetate. There is thus obtained a first crop (11.7 g.; m.p. 248°–249° C.) and a second crop (2.3 g.; m.p. 244°–246° C.) of 1,3-dehydro-7-chloro-5-(2,6-difluorophenyl)-2H-1,4-benzodiazepin-2-one (VI).

Anal. Calcd. for $C_{15}H_9ClF_2N_2O$: C, 58.74; H, 2.96; Cl, 11.56; F, 12.39; N, 9.14. Found: C, 58.89; H, 2.78; Cl, 11.39; F, 11.72; N, 8.95.

This material contains 1.9% ethyl acetate of solvation. Recrystallization of the solvated material from ethanol provides unsolvated 1,3-dihydro-7-chloro-5-(2,6-difluorophenyl)2H-1,4-benzodiazepin-2-one.

PREPARATION 2

1,3-Dihydro-7-chloro-5-(2,6-difluorophenyl)-2H-1,4-benzodiazepine-2-thione (V)

A solution of 7.65 g. (0.025 mole) of 1,3-dihydro-7-chloro-5-(2,6-difluorophenyl)-2H-1,4-benzodiazepin-2-one in 500 ml. of pyridine is treated with 5.55 g. (0.025 mole) of phosphorus pentasulfide and heated under reflux in a nitrogen atmosphere for two hours. The pyridine (350 ml.) is removed in vacuo and the thus-produced residue is poured onto crushed ice. The aqueous phase is extracted with methylene chloride and then discarded. The extract is washed successively with three 200-ml. portions of water and 100 ml. of brine, and dried over anhydrous sodium sulfate. Removal of the solvent gives 7.0 g. of solid which is recrystallized from ethanol-water, to give in 2 crops, 6.8 g. of crude material which, after recrystallization from ethanolwater, gives pure 1,3-dihydro-7-chloro-5-(2,6-difluorophenyl)-2H-1,4-benzodiazepine-2-thione, m.p. 222.5°–224° C.

Anal. Calcd. for $C_{15}H_9ClF_2N_2S$: C, 55.82; H, 2.81; Cl, 10.98; F, 11.77; N, 8.68; S, 9.93. Found: C, 56.13; H, 2.68; Cl, 11.13; F, 11.69; N, 8.40; S, 9.84.

PREPARATION 3

1,3-Dihydro-7-(trifluoromethyl)-5-phenyl-2H-1,4-benzodiazepine-2-thione (V)

A stirred mixture of 1,3-dihydro-7-trifluoromethyl-5-phenyl-2H-1,4-benzodiazepin-2-one (89.7 g.; 0.294 mole), dry pyridine (2300 ml.) and phosphorus pentasulfide (72.4 g.; 0.323 mole) is refluxed under nitrogen for 30 minutes, cooled and concentrated in vacuo. A suspension of the residue in ice water is extracted with methylene chloride. The extract is dried over anhydrous potassium carbonate and concentrated. The residue thus obtained is crystallized from methylene chloride-ethanol to give 43.2 g., m.p. 228.5°–229° C. (dec.) and 17.8 g., m.p. 229°–230° C. (dec.) (64.5%) of 1,3-dihydro-7-(trifluoromethyl)-5-phenyl-2H-1,4-benzodiazepine-2-thione; an analytical sample prepared by recrystallization from methylene chloride-ethanol has a melting point of 223.5° C. (dec.).

Anal. Calcd. for $C_{16}H_{11}F_3N_2S$: C, 60.00; H, 3.46; F, 17.79; N, 8.75; S, 10.01. Found: C, 59.85; H, 3.73; F, 17.83; N, 8.42; S, 10.26.

PREPARATION 4

7-Chloro-1,3-dihydro-3-methyl-5-phenyl-2H1,4-benzodiazepine-2-thione (V)

A stirred mixture of 7-chloro-1,3-dihydro-3-methyl-5-phenyl-2H-1,4-benzodiazepin-2-one (0.294 mole), dry pyridine (2300 ml.) and phosphorus pentasulfide (72.4 g.; 0.323 mole) is reflexed under nitrogen for 30 minutes, cooled and concentrated in vacuo. A suspension of the residue in ice water is extracted with methylene chloride. The extract is dried over anhydrous potassium carbonate and concentrated. The residue thus obtained is crystallized from methylene chlorideethanol to give 7-chloro-1,3-dihydro-3-methyl-5-phenyl-2H-1,4-benzodiazepine-2-thione.

PREPARATION 5

1,3-Dihydro-7-chloro-5-(2-chlorophenyl)-2H-1,4-benzodiazepine-2-thione (V)

A solution of (0.025 mole) of 1,3-dihydro-7-chloro-5-(2-chlorophenyl)-2H-1,4-benzodiazepin-2-one in about 500 ml. of pyridine is treated with 5.55 g. (0.025 mole) of phosphorus pentasulfide and heated under reflux in a nitrogen atmosphere for 2 hours. The pyridine is removed in vacuo and the thus-produced residue is poured onto crushed ice. The aqueous phase is extracted with methylene chloride and then discarded. The extract is washed successively with three 200-ml. portions of water and 100 ml. of brine, and dried over anhydrous sodium sulfate. Removal of the solvent gives a solid which is recrystallized from ethanol-water, to give crude material which, after recrystallization from ethanolwater, gives pure 1,3-dihydro-7-chloro-5-(2-chlorophenyl)-2H-1,4-benzodiazepine-2-thione, melting point 251°–253° C.

PREPARATION 6

7-bromo-1,3-dihydro-5-(2-pyridyl)-2H-1,4-benzodiazepine-2-thione (V)

A stirred solution of 6.53 g. of 7-bromo-1,3-dihydro-5-(2-pyridyl)-2H-1,4-benzodiazepin-2-one (prepared as in J. Pharm. Sci. 53, 264) in 400 ml. of dry pyridine is heated in an oil bath, under nitrogen, with 5.05 g. of phosphorus pentasulfide at between about 110° to 120° C. for about 1 hour, cooled and concentrated under vacuum. Pyridine remaining in the residue is removed by the successive addition of xylene and toluene with vacuum concentration after each addition of solvent. The dark brown solid residue is triturated with a mixture of aqueous sodium carbonate solution and chloroform and the resulting finely divided tán solid is collected by filtration, washed with water, dissolved in a mixture of chloroform and ethanol, decolorized with activated carbon and crystallized to yield 3.39 g. of product melting at 249° C. (with decomposition) and 0.559 g. melting at 243° C. (with decomposition). The analytical sample is crystallized from ethanol to give pure 7-bromo-1,3-dihydro-5-(2-pyridyl)-2H-1,4-benzodiazepine-2-thione, with a melting point of 245° to 246° C. (with decomposition) and ultraviolet (ethanol) end absorption, $\mu$max 219 mu ($\epsilon$=24,100).

Anal. Calcd. for $C_{14}H_{10}BrN_3S$: C, 50.61; H, 3.03; Br, 24.06; N, 12.65; S, 9.65. Found: C, 49.82; H, 3.31; Br, 24.31; N, 12.60; S, 9.59.

PREPARATION 7

7-Chloro-1,3-dihydro-5-methyl-2H-1,4-benzodiazepine-2-thione (V)

To a hot solution of 1 g. (5 mm. les) of 7-chloro-1,3-dihydro-5-methyl-2H-1,4-benzodiazepin-2-one (prepared as in French Pat. No. 1,391,752) in 150 ml. of xylene, 1.1 g. (5 mmoles) of phosphorus pentasulfide is added. The mixture is heated under reflux in a nitrogen atmosphere for about 4 hours. The reaction mixture is cooled and filtered, with the filtrate containing only a small amount of material. The filtered solid is treated with hot water and filtered again. The filtrate is treated with 20% sodium hydroxide to give a pH of 6 to 8 and the white solid removed by extraction with ethyl acetate to give 129 ml. of crude product. The initial solid is again treated with water, the aqueous phase made base with sodium bicarbonate and then extracted with hot ethyl acetate to give 1 g. of brown solid. This material plus the 129 mg. of crude product are chromatographed on 130 g. of silica gel (silicic acid) using 50% ethyl acetate: 50% cyclohexane as eluting solvent. The product taken from the column is recrystallized from ethyl acetate to give 455 mg. of 7-chloro-1,3-dihydro-5-methyl-2H-1,4-benzodiazepine-2-thione (V), having a melting point of 205° to 206° C. (with decomposition). A previously prepared sample of the product, 7-chloro-1,3-dihydro-5-methyl-2H-1,4-benzodiazepine-2-thione, melts at 201° to 203° C. and gives the analysis that follows.

Anal. Calcd. for $C_{10}H_9ClN_2S$: C, 53.45; H, 4.04; N, 12.47; Cl, 15.78; S, 14.27. Found: C, 53.29; H, 3.87; N, 12.16; Cl, 15.88; S, 14.67.

EXAMPLE 1

7-chloro-5-phenyl-2-(2-propynylamino)-3H-1,4-benzodiazepine (IV)

A mixture of 8.3 g. of 7-chloro-1,3-dihydro-5-phenyl-2H-1,4-benzodiazepine-2-thione (V), 8.3 g. of propargyl amine (2-propynylamine) and 130 ml. of dry THF is stirred, under nitrogen, at ambient temperature for about 5 hours and then concentrated in vacuo. The residue thus obtained is crystallized from methanol to give 7.9 g. of 7-chloro-5-phenyl-2-(2-propynylamino)-3H-1,4-benzodiazepine, m.p. 201.5°–202° C., an analytical sample prepared by recrystallization from methanol melts at 203.5°–205° C.

Anal. Calcd. for $C_{18}H_{14}ClN_3$: C, 70.24; H, 4.58; Cl, 11.52; N, 13.65. Found: C, 69.90; H, 4.56; Cl, 11.57; N, 13.35.

EXAMPLE 2

7-chloro-5-(2-chlorophenyl-2-(2-propynylamino)-3H-1,4-benzodiazepine (IV)

A mixture of 15.0 g. (0.0467 mole) of 7-chloro-5-(2-chlorophenyl)-1,3-dihydro-2H-1,4-benzodiazepine-2-thione (V), 15.0 g. (0.272 mole) of propargyl amine and 180 ml. of tetrahydrofuran is stirred, under nitrogen for about 4 hours and concentrated in vacuo. This residue thus obtained is dissolved in methanol decolorized with activated charcoal and crystallized to give 7.53 g. of 7-chloro-5-(2-chlorophenyl)-2-(2-propynyiamino)-3H-1,4-benzodiazepine, m.p. 165°–166.5° C. and 2.65 g. of additional product, m.p. 164°–165.5° C.

Anal. Calcd. for $C_{18}H_{13}Cl_2N_3$: C, 63.17; H, 3.83; Cl, 20.72; N, 12.28. Found: C, 63.06; H, 3.72; Cl, 20.87; N, 12.33.

EXAMPLE 3

7-chloro-5-(2,6-difluorophenyl)-2-(2-butynylamino)-3H-1,4-benzodiazepine (IV)

A mixture of 10.0 g. of 7-chloro-1,3-dihydro-5-(2,6-difluorophenyl)-2H-1,4-benzodiazepine-2-thione (V), 10.0 g. of 2-butynylamine, and 150 ml. of dry tetrahydrofuran is stirred under nitrogen at ambient temperature for about 5 hours and then concentrated in vacuo. The residue thus obtained is recrystallized from methanol to give 7-chloro-5-(2,6-difluorophenyl)-2-(2-butynylamino)-3H-1,4-benzodiazepine.

EXAMPLE 4

7-trifluoromethyl-5-phenyl-2-(2-pentynylamino)-3H-1,4-benzodiazepine (IV)

A mixture of 10.0 g. of 1,3-dihydro-7-(trifluoromethyl)-5-phenyl-2H-1,4-benzodiazepine-2-thione (V), 10.0 g. of 2-pentynylamine, and 150 ml. of dry tetrahydrofuran is stirred under nitrogen at ambient temperature for about 5 hours and then concentrated in vacuo. The residue thus obtained is recrystallized from methanol to give 7-trifluoromethyl-5-phenyl-2-(2-pentynylamino)-3H-1,4-benzodiazepine.

EXAMPLE 5

7-bromo-5-(2-pyridyl)-2-(2-propynylamino)-3H-1,4-benzodiazepine (IV)

A mixture of 10.0 g. of 7-bromo-1,3-dihydro-5-(2-pyridyl)-2H-1,4-benzodiazepine-2-thione (V), 10.0 g. of propargyl amine, and 150 ml. of dry tetrahydrofuran is stirred under nitrogen at ambient temperature for about 5 hours and then concentrated in vacuo. The residue thus obtained is recrystallized from methanol to give 7-bromo-5-(2-pyridyl)-2-(2-propynylamino)-3H-1,4-benzodiazepine.

EXAMPLE 6

7-chloro-5-methyl-2-[(1-methyl-2-pentynyl)amino]-3H-1,4-benzodiazepine (IV)

A mixture of 10.0 g. of 7-chloro-1,3-dihydro-5-methyl-2H-1,4-benzodiazepine-2-thione (V), 10.0 g. of 1-methyl-2-pentynylamine, and 150 ml. of dry tetrahydrofuran is stirred under nitrogen at ambient temperature for about 5 hours and then concentrated in vacuo. The residue thus obtained is recrystallized from methanol to give 7-chloro-5-methyl-2-[(1-methyl-2-pentynyl)amino]-3H-1,4-benzodiazepine.

EXAMPLE 7

7-chloro-3-methyl-5-phenyl-2-[(1-methyl-2-propynyl)amino]-3H-1,4-benzodiazepine (IV)

A mixture of 10.0 g. of 7-chloro-1,3-dihydro-3-methyl-5-phenyl-2H-1,4-benzodiazepine-2-thione (V), 10.0 g. of 1-methyl-2-propynylamine, and 150 ml. of dry tetrahydrofuran is stirred under nitrogen at ambient temperature for about 5 hours and then concentrated in vacuo. The residue thus obtained is recrystallized from methanol to give 7-chloro-3-methyl-5-phenyl-2-[(1-methyl-2-propynyl)amino]-3H-1,4-benzodiazepine.

EXAMPLE 8

7-chloro-5-(2-chlorophenyl)-2-[(1-methyl-2-propynyl)amino]-3H-1,4-benzodiazepine (IV)

A mixture of 10.0 g. of 7-chloro-5-(2-chlorophenyl)-1,3-dihydro-2H-1,4-benzodiazepine-2thione (V), 10.0 g. of 1-methyl-2-propynylamine, and 150 ml. of dry tetrahydrofuran is stirred under nitrogen at ambient temperature for about 5 hours and then concentrated in vacuo. The residue thus obtained is recrystallized from methanol to give 7-chloro-5-(2-chlorophenyl)-2-[(1-methyl-2-propynyl)amino]-3H-1,4-benzodiazepine.

In the manner given in Example 1-8, above, other 1,3-dihydro-2H-1,4-benzodiazepine-2-thiones of formula V, can be condensed with the appropriate 2-alkynylamine of formula VII, to obtain the other 2-(2-alkynylamino)-3H-1,4-benzodiazepines of formula IV. For example, the following 1,3-dihydro-2H-1,4-benzodiazepine-2-thiones:

7-bromo-1,3-dihydro-5-phenyl-2H-1,4-benzodiazepine-2-thione;
7-fluoro-1,3-dihydro-5-phenyl-2H-1,4-benzodiazepine-2-thione;
7-nitro-1,3-dihydro-5-phenyl-2H-1,4-benzodiazepine-2-thione;
7-trifluoromethyl-1,3-dihydro-5-phenyl-2H-1,4-benzodiazepine-2-thione;
7-cyano-1,3-dihydro-5-phenyl-2H-1,4-benzodiazepine-2-thione;
7-methylthio-1,3-dihydro-5-phenyl-2H-1,4-benzodiazepine-2-thione;
7-bromo-1,3-dihydro-5-(2-chlorophenyl)-2H-1,4-benzodiazepine-2-thione;
7-fluoro-1,3-dihydro-5-(2-chlorophenyl)-2H-1,4-benzodiazepine-2-thione;
7-nitro-1,3-dihydro-5-(2-chlorophenyl)-2H-1,4-benzodiazepine-2-thione;
7-trifluoromethyl-1,3-dihydro-5-(2-chlorophenyl)-2H-1,4-benzodiazepine-2-thione;
7-cyano-1,3-dihydro-5-(2-chlorophenyl)-2H-1,4-benzodiazepine-2-thione;
7-methylthio-1,3-dihydro-5-(2-chlorophenyl)-2H-1,4-benzodiazepine-2-thione;
7-chloro-1,3-dihydro-5-(2-fluorophenyl)-2H-1,4-benzodiazepine-2-thione;
7-bromo-1,3-dihydro-5-(2-fluorophenyl)-2H-1,4-benzodiazepine-2-thione;
7-fluoro-1,3-dihydro-5-(2-fluorophenyl)-2H-1,4-benzodiazepine-2-thione;
7-nitro-1,3-dihydro-5-(2-fluorophenyl)-2H-1,4-benzodiazepine-2-thione;
7-trifluoromethyl-1,3-dihydro-5-(2-fluorophenyl)-2H-1,4-benzodiazepine-2-thione;
7-cyano-1,3-dihydro-5-(2-fluorophenyl)-2H-1,4-benzodiazepine-2-thione;
7-methylthio-1,3-dihydro-5-(2-fluorophenyl)-2H-1,4-benzodiazepine-2-thione;
7-chloro-1,3-dihydro-5-(2-pyrimidyl)-2H-1,4-benzodiazepine-2-thione;
7-bromo-1,3-dihydro-5-(2-furyl)-2H-1,4-benzodiazepine-2-thione;
7-fluoro-1,3-dihydro-5-(2-pyrryl)-2H-1,4-benzodiazepine-2-thione;
7-nitro-1,3-dihydro-5-(2-thienyl)-2H-1,4-benzodiazepine-2-thione;
7-trifluoromethyl-1,3-dihydro-5-cyclohexyl-2H-1,4-benzodiazepine-2-thione;
7-cyano-1,3-dihydro-5-(1-cyclohexenyl)-2H-1,4-benzodiazepine-2-thione;
7-methylthio-1,3-dihydro-5-methyl-2H-1,4-benzodiazepine-2-thione; and the like; can be reacted with 2-propynylamine (propargyl amine) to obtain:

7-bromo-5-phenyl-2-(2-propynylamino)-3H-1,4-benzodiazepine;
7-fluoro-5-phenyl-2-(2-propynylamino)-3H-1,4-benzodiazepine;
7-nitro-5-phenyl-2-(2-propynylamino)-3H-1,4-benzodiazepine;

7-trifluoromethyl-5-phenyl-2-(2-propynylamino)-3H-1,4-benzodiazepine;
7-cyano-5-phenyl-2-(2-propynylamino)-3H-1,4-benzodiazepine;
7-methylthio-5-phenyl-2-(2-propynylamino)-3H-1,4-benzodiazepine;
7-bromo-5-(2-chlorophenyl)-2-(2-propynylamino)-3H-1,4-benzodiazepine;
7-fluoro-5-(2-chlorophenyl)-2-(2-propynylamino)-3H-1,4-benzodiazepine;
7-nitro-5-(2-chlorophenyl)-2-(2-propynylamino)-3H-1,4-benzodiazepine;
7-trifluoromethyl-5-(2-chlorophenyl)-2-(2-propynylamino)-3H-1,4-benzodiazepine;
7-cyano-5-(2-chlorophenyl)-2-(2-propynylamino)-3H-1,4-benzodiazepine;
7-methylthio-5-(2-chlorophenyl)-2-(2-propynylamino)-3H-1,4-benzodiazepine;
7-chloro-5-(2-fluorophenyl)-2-(2-propynylamino)-3H-1,4-benzodiazepine;
7-bromo-5-(2-fluorophenyl)-2-(2-propynylamino)-3H-1,4-benzodiazepine;
7-fluoro-5-(2-fluorophenyl)-2-(2-propynylamino)-3H-1,4-benzodiazepine;
7-nitro-5-(2-fluorophenyl)-2-(2-propynylamino)-3H-1,4-benzodiazepine;
7-trifluoromethyl-5-(2-fluorophenyl)-2-(2-propynylamino)-3H-1,4-benzodiazepine;
7-cyano-5-(2-fluoromethyl)-2-(2-propynylamino)-3H-1,4-benzodiazepine;
7-methylthio-5-(2-fluorophenyl)-2-(2-propynylamino)-3H-1,4-benzodiazepine;
7-chloro-5-(2-pyrimidyl)-2-(2-propynylamino)-3H-1,4-benzodiazepine;
7-bromo-5-(2-furyl)-2-(2-propynylamino)-3H-1,4-benzodiazepine;
7-fluoro-5-(2-pyrryl)-2-(2-propynylamino)-3H-1,4-benzodiazepine;
7-nitro-5-(2-thienyl)-2-(2-propynylamino)-3H-1,4-benzodiazepine;
7-trifluoromethyl-5-cyclohexyl-2-(2-propynylamino)-3H-1,4-benzodiazepine;
7-cyano-5-(1-cyclohexenyl)-2-(2-propynylamino)-3H-1,4-benzodiazepine;
7-methylthio-5-methyl-2-(2-propynylamino)-3H-1,4-benzodiazepine; respectively, and the like.

In the same manner the 2-thiones named above can be reacted with 1-methyl-2-propynylamine to obtain:
7-bromo-5-phenyl-2-[(1-methyl-2-propynyl)amino]-3H-1,4-benzodiazepine;
7-fluoro-5-phenyl-2-[(1-methyl-2-propynyl)amino]-3H-1,4-benzodiazepine;
7-nitro-5-phenyl-2-[(1-methyl-2-propynyl)amino]-3H-1,4-benzodiazepine;
7-trifluoromethyl-5-phenyl-2-[(1-methyl-2-propynyl]-3H-1,4-benzodiazepine;
7-cyano-5-phenyl-2-[(1-methyl-2-propynyl)amino]-3H-1,4-benzodiazepine;
7-methylthio-5-phenyl-2-[(1-methyl-2-propynyl)amino]-3H-1,4-benzodiazepine;
7-bromo-5-(2-chlorophenyl)-2-[(1-methyl-2-propynyl)amino]-3H-1,4-benzodiazepine;
7-fluoro-5-(2-chlorophenyl)-2-[(1-methyl-2-propynyl)amino]-3H-1,4-benzodiazepine;
7-nitro-5-(2-chlorophenyl)-2-[(1-methyl-2-propynyl)amino]-3H-1,4-benzodiazepine;
7-trifluoromethyl-5-(2-chlorophenyl)-2-[(1-methyl-2-propynyl)amino]-3H-1,4-benzodiazepine;
7-cyano-5-(2-chlorophenyl-2-[(1-methyl-2-propynyl)amino]-3H-1,4-benzodiazepine;
7-methylthio-5-(2-chlorophenyl)-2-[(1-methyl-2-propynyl)amino]-3H-1,4-benzodiazepine;
7-chloro-5-(2-fluorophenyl)-2-[(1-methyl-2-propynyl)-amino]-3H-1,4-benzodiazepine;
7-bromo-5-(2-fluorophenyl)-2-[(1-methyl-2-propynyl)-amino]-3H-1,4-benzodiazepine;
7-fluoro-5-(2-fluorophenyl)-2-[(1-methyl-2-propynyl)-amino]-3H-1,4-benzodiazepine;
7-nitro-5-(2-fluorophenyl)-2-[(1-methyl-2-propynyl)-amino]-3H-1,4-benzodiazepine;
7-trifluoromethyl-5-(2-fluorophenyl)-2-[(1-methyl-2-propynyl)amino]-3H-1,4-benzodiazepine;
7-cyano-5-(2-fluorophenyl)-2-[(1-methyl-2-propynyl)-amino]-3H-1,4-benzodiazepine;
7-methylthio-5-(2-fluorophenyl)-2-[(1-methyl-2-propynyl)amino]-3H-1,4-benzodiazepine;
7-chloro-5-(2-pyrimidyl)-2-[(1-methyl-2-propynyl)-amino-3H-1,4-benzodiazepine;
7-bromo-5-(2-furyl)-2-[(1-methyl-2-propynyl)amino]-3H-1,4-benzodiazepine;
7-fluoro-5-(2-pyrryl)-2-[(1-methyl-2-propynyl)amino]-3H-1,4-benzodiazepine;
7-nitro-5-(2-thienyl)-2-[(1-methyl-2-propynyl)amino]-3H-1,4-benzodiazepine;
7-trifluoromethyl-5-cyclohexyl-2-[(1-methyl-2-propynyl)amino]-3H-1,4-benzodiazepine;
7-cyano-5-(1-cyclohexenyl)-2-[(1-methyl-2-propynyl)-amino]-3H-1,4-benzodiazepine;
7-methylthio-5-methyl-2-[(1-methyl-2-propynyl)amino]-3H-1,4-benzodiazepine; and the like.

Similarly the other 2-alkynylamines, hereinbefore listed, can likewise be used to obtain the corresponding 2-alkynylamino-3H-1,4-benzodiazepines.

EXAMPLE 9

8-chloro-1-methyl-6-phenyl-4H-imidazo[1,2-a]-[1,4]benzodiazepine(Ia)

To a 29.5 ml. of ice cold 50% (weight) sulfuric acid is added successively with stirring 9.1 g. (0.0295 mole) of 7-chloro-5-phenyl-2-(2-propynylamino)-3H-1,4-benzodiazepine (IV) and 0.388 g. of mercuric sulfate. The resulting mixture is stirred at ambient temperature for about 18 hours; poured into ice-water, neutralized with sodium hydroxide and extracted with chloroform. The extract thus obtained, is dried over potassium carbonate and concentrated in vacuo. The residue thus obtained, is chromatographed on 450 g. of silica gel with chloroform containing 1% methanol. The product thus obtained is crystallized from ethyl acetate-Skellysolve B hexanes to give 4.93 g. of 8-chloro-1-methyl-6-phenyl-4H-imidazo[1,2-a][1,4]benzodiazepine, an analytical sample of which melted at 192°–193° C.; λmax 222 mμ (ε=37,300), 255 (inflection, 13,100), λmax 310 mμ (ε=1,280).

Anal. Calcd. for $C_{18}H_{14}ClN_3$: C, 70.24; H, 4.58; Cl, 11.52; N, 13.65. Found: C, 70.15; H, 4.59; Cl, 11.55; N, 13.80.

EXAMPLE 10

8-chloro-6-(2-chlorophenyl)-1-methyl-4H-imidazo[1,2-a][1,4]benzodiazepine (Ia)

To 10 ml. of ice cold 50% (weight) sulfuric acid is added successively with stirring under nitrogen, 3.42 g. (0.01 mole) of 7-chloro-5-(2-chlorophenyl)-2-(2-propynylamino)-3H-1,4-benzodiazepine (IV) and 0.132 g. of mercuric sulfate. The mixture is stirred at ambient temperature for about 18 hours and then poured into ice-water. The resulting mixture is made alkaline with 15% aqueous sodium hydroxide solution and extracted with chloroform. The chloroform extract is dried over potassium carbonate and concentrated in vacuo and the residue thus obtained is crystallized from ethyl acetate-Skellysolve B hexanes to give 0.95 g. of 8-chloro-6-(2-chlorophenyl)-1-methyl-4H-imidazo[1,2-a][1,4] benzodiazepine; an analytical sample of which melted at 148° to 149° C.

Anal. Calcd. for $C_{18}H_{13}Cl_2N_3$: C, 63.17; H, 3.83; Cl, 20.72; N, 12.28. Found: C, 62.85; H, 3.83; Cl, 20.81; N, 12.38.

EXAMPLE 11

8-chloro-6-(2,6-difluorophenyl)-1-ethyl-4H-imidazo[1,2-a][1,4]benzodiazepine (Ia)

To 10 ml. of ice cold 50% (wt) sulfuric acid is added successively with stirring under nitrogen 0.01 mole of 7-chloro-5-(2,6-difluorophenyl)-2-(2-butynylamino)-3H-1,4-benzodiazepine (IV) and 0.132 g. of mercuric sulfate. The resulting mixture is stirred for about 18 hours, poured into ice water, neutralized with 15% aqueous sodium hydroxide solution and extracted with chloroform. The extract thus obtained is dried over potassium carbonate and concentrated in vacuo. The residue thus obtained is chromatographed on silica gel with chloroform containing 1% methanol. The eluates containing the desired product are combined, concentrated in vacuo and crystallized from ethyl acetate-hexanes to give 8-chloro-6-(2,6-difluorophenyl)-1-ethyl-4H-imidazo[1,2-a][1,4]benzodiazepine.

EXAMPLE 12

8-trifluoromethyl-6-phenyl-1-propyl-4H-imidazo[1,2-a][1,4]benzodiazepine (Ia)

To 10 ml. of ice cold 50% (wt) sulfuric acid is added successively with stirring under nitrogen 0.01 mole of 7-trifluoro-methyl-5-phenyl-2-(2-pentynylamino)-3H-1,4-benzodiazepine (IV) and 0.132 g. of mercuric sulfate. The resulting mixture is stirred for about 18 hours, poured into ice water, neutralized with 15% aqueous sodium hydroxide solution and extracted with chloroform. The extract thus obtained is dried over potassium carbonate and concentrated in vacuo. The residue thus obtained is chromatographed on silica gel with chloroform containing 1% methanol. The eluates containing the desired product are combined, concentrated in vacuo and crystallized from ethyl acetate-hexanes to give 8-trifluoromethyl-6-phenyl-1-propyl-4H-imidazo[1,2-a][1,4]benzodiazepine.

EXAMPLE 13

8-bromo-1-methyl-6-(2-pyridyl)-4H-imidazo[1,2-a][1,4]benzodiazepine (Ia)

To 10 ml. of ice cold 50% (wt) sulfuric acid is added successively with stirring under nitrogen 0.01 mole of 7-bromo-5-(2-pyridyl)-2-(2-propynylamino)-3H-1,4-benzodiazepine (IV) and 0.132 g. of mercuric sulfate. The resulting mixture is stirred for about 18 hours, poured into ice water, neutralized with 15% aqueous sodium hydroxide solution and extracted with chloroform. The extract thus obtained is dried over potassium carbonate and concentrated in vacuo. The residue thus obtained is chromatographed on silica gel with chloroform containing 1% methanol. The eluates containing the desired product are combined, concentrated in vacuo and crystallized from ethyl acetate-hexanes to give 8-bromo-1-methyl-6-(2-pyridyl)-4H-imidazo[1,2-a][1,4]benzodiazepine.

EXAMPLE 14

8-chloro-2,6-dimethyl-1-propyl-4H-imidazo[1,2-a][1,4]benzodiazepine (Ia)

To 10 ml. of ice cold 50% (wt) sulfuric acid is added successively with stirring under nitrogen 0.01 mole of 7-chloro-5-methyl-2-[(1-methyl-2-pentynyl)amino]-3H-1,4-benzodiazepine (IV) and 0.132 g. of mercuric sulfate. The resulting mixture is stirred for about 18 hours, poured into ice water, neutralized with 15% aqueous sodium hydroxide solution and extracted with chloroform. The extract thus obtained is dried over potassium carbonate and concentrated in vacuo. The residue thus obtained is chromatographed on silica gel with chloroform containing 1% methanol. The eluates containing the desired product are combined, concentrated in vacuo and crystallized from ethyl acetate-hexanes to give 8-chloro-2,6-dimethyl-1-propyl-4H-imidazo[1,2-a][1,4]benzodiazepine.

EXAMPLE 15

8-chloro-1,2,4-trimethyl-6-phenyl-4H-imidazo[1,2-a][1,4]benzodiazepine (Ia)

To 10 ml. of ice cold 50% (wt) sulfuric acid is added successively with stirring under nitrogen 0.01 mole of 7-chloro-3-methyl-5-phenyl-2-[(1-methyl-2-propynyl)-amino]-3H-1,4-benzodiazepine (IV) and 0.132 g. of mercuric sulfate. The resulting mixture is stirred for about 18 hours, poured into ice water, neutralized with 15% aqueous sodium hydroxide solution and extracted with chloroform. The extract thus obtained is dried over potassium carbonate and concentrated in vacuo. The residue thus obtained is chromatographed on silica gel with chloroform containing 1% methanol. The eluates containing the desired product are combined, concentrated in vacuo and crystallized from ethyl acetate-hexanes to give 8-chloro-1,2,4-trimethyl-6-phenyl-4H-imidazo[1,2-a][1,4]benzodiazepine.

EXAMPLE 16

8-chloro-1,2-dimethyl-6-(2-chlorophenyl)-4H-imidazo[1,2-a][1,4]benzodiazepine (Ia)

To 10 ml. of ice cold 50% (wt) sulfuric acid is added successively with stirring under nitrogen 0.01 mole of 7-chloro-5-(2-chlorophenyl)-2-[(1-methyl-2-propynyl)amino]-3H-1,4-benzodiazepine (IV) and 0.132 g. of mercuric sulfate. The resulting mixture is stirred for about 18 hours, poured into ice water, neutralized with 15% aqueous sodium hydroxide solution and extracted with chloroform. The extract thus obtained is dried over potassium carbonate and concentrated in vacuo. The residue thus obtained is chromatographed on silica gel with chloroform containing 1% methanol. The eluates containing the desired product are combined, concentrated in vacuo and crystallized from ethyl acetate-hexanes to give 8-chloro-1,2-dimethyl-6-(2-chlorophenyl)-4H-imidazo[1,2-a][1,4]benzodiazepine.

In the manner given in Examples 9–16, above, other 2-(2-alkynylamino)-3H-1,4-benzodiazepines of formula IV, for example those prepared and listed in Example 8, above, can be subjected to ring closure to obtain the corresponding 1-alkyl-4H-imidazo[1,2-a][1,4]benzodiazepines of formula Ia, respectively, such as:

8-bromo-6-phenyl-1-methyl-4H-imidazo[1,2-a][1,4]benzodiazepine;
8-fluoro-6-phenyl-1-methyl-4H-imidazo[1,2-a][1,4]benzodiazepine;
8-nitro-6-phenyl-1-methyl-4H-imidazo[1,2-a][1,4]benzodiazepine;
8-trifluoromethyl-6-phenyl-1-methyl-4H-imidazo[1,2-a][1,4]benzodiazepine;
8-cyano-6-phenyl-1-methyl-4H-imidazo[1,2-a][1,4]benzodiazepine;
8-methylthio-6-phenyl-1-methyl-4H-imidazo[1,2-a][1,4]benzodiazepine;
8-bromo-6-(2-chlorophenyl)-1-methyl-4H-imidazo[1,2-a][1,4]benzodiazepine;
8-fluoro-6-(2-chlorophenyl)-1-methyl-4H-imidazo[1,2-a][1,4]benzodiazepine;
8-nitro-6-(2-chlorophenyl)-1-methyl-4H-imidazo[1,2-a][1,4]benzodiazepine;
8-trifluoromethyl-6-(2-chlorophenyl)-1-methyl-4H-imidazo[1,2-a][1,4]benzodiazepine;
8-cyano-6-(2-chlorophenyl)-1-methyl-4H-imidazo[1,2-a][1,4]benzodiazepine;
8-methylthio-6-(2-chlorophenyl)-1-methyl-4H-imidazo[1,2-a][1,4-benzodiazepine;
8-chloro-6-(2-fluorophenyl)-1-methyl-4H-imidazo[1,2-a][1,4]benzodiazepine;
8-bromo-6-(2-fluorophenyl)-1-methyl-4H-imidazo[1,2-a][1,4]benzodiazepine;
8-fluoro-6-(2-fluorophenyl)-1-methyl-4H-imidazo[1,2-a][1,4]benzodiazepine;
8-nitro-6-(2-fluorophenyl)-1-methyl-4H-imidazo[1,2-a][1,4]benzodiazepine;
8-trifluoromethyl-6-(2-fluorophenyl)-1-methyl-4H-imidazo[1,2-a][1,4]benzodiazepine;
8-cyano-6-(2-fluorophenyl)-1-methyl-4H-imidazo[1,2-a][1,4]benzodiazepine;
8-methylthio-6-(2-fluorophenyl)-1-methyl-4H-imidazo[1,2-a][1,4]benzodiazepine;
8-chloro-6-(2-pyrimidyl)-1-methyl-4H-imidazo[1,2-a][1,4]benzodiazepine;
8-bromo-6-(2-furyl)-1-methyl-4H-imidazo[1,2-a][1,4]-benzodiazepine;
8-fluoro-6-(2-pyrryl)-1-methyl-4H-imidazo[1,2-a][1,4]benzodiazepine;
8-nitro-6-(2-thienyl)-1-methyl-4H-imidazo[1,2-a][1,4benzodiazepine;
8-trifluoromethyl-6-cyclohexyl-1-methyl-4H-imidazo[1,2-a][1,4]benzodiazepine;
8-cyano-6-(1-cyclohexenyl)-1-methyl-4H-imidazo[1,2-a][1,4]benzodiazepine;
8-methylthio-1,6-dimethyl-4H-imidazo[1,2-a][1,4]benzodiazepine;
8-bromo-6-phenyl-1,2-dimethyl-4H-imidazo[1,2-a][1,4]benzodiazepine;
8-fluoro-6-phenyl-1,2-dimethyl-4H-imidazo[1,2-a][1,4]benzodiazepine;
8nitro-6-phenyl-1,2-dimethyl-4H-imidazo[1,2-a][1,4]benzodiazepine;
8-trifluoromethyl-6-phenyl-1,2-dimethyl-4H-imidazo[1,2-a][1,4]benzodiazepine;
8-cyano-6-phenyl-1,2-dimethyl-4H-imidazo[1,2-a][1,4]benzodiazepine;
8-methylthio-6-phenyl-1,2-dimethyl-4H-imidazo[1,2-a][1,4]benzodiazepine;
8-bromo-6-(2-chlorophenyl)-1,2-dimethyl-4H-imidazo[1,2-a][1,4]benzodiazepine;
8-fluoro-6-(2-chlorophenyl)-1,2-dimethyl-4H-imidazo[1,2-a][1,4]benzodiazepine;
8-nitro-6-(2-chlorophenyl)-1,2-dimethyl-4H-imidazo[1,2-a][1,4]benzodiazepine;
8-trifluoromethyl-6-(2-chlorophenyl)-1,2-dimethyl-4H-imidazo[1,2-a][1,4]benzodiazepine;
8-cyano-6-(2-chlorophenyl)-1,2-dimethyl-4H-imidazo[1,2-a][1,4]benzodiazepine;
8-methylthio-6-(2-chlorophenyl)-1,2-dimethyl-4H-imidazo[1,2-a][1,4]benzodiazepine;
8-chloro-6-(2-fluorophenyl)-1,2-dimethyl-4H-imidazo[1,2-a][1,4]benzodiazepine;
8-bromo-6-(2-fluorophenyl)-1,2-dimethyl-4H-imidazo[1,2-a][1,4]benzodiazepine;
8-fluoro-6-(2-fluorophenyl)-1,2-dimethyl-4H-imidazo[1,2-a][1,4]benzodiazepine;
8-nitro-6-(2-fluorophenyl)-1,2-dimethyl-4H-imidazo[1,2-a][1,4]benzodiazepine;
8-trifluoromethyl-6-(2-fluorophenyl)-1,2-dimethyl-4H-imidazo[1,2-a][1,4]benzodiazepine;
8-cyano-6-(2-fluorophenyl)-1,2-dimethyl-4H-imidazo[1,2-a][1,4]benzodiazepine;
8-methylthio-6-(2-fluorophenyl)-1,2-dimethyl-4H-imidazo[1,2-a][1,4]benzodiazepine;
8-chloro-6-(2-pyrimidyl)-1,2-dimethyl-4H-imidazo[1,2-a]-[1,4]benzodiazepine;
8-bromo-6-(2-furyl)-1,2-dimethyl-4H-imidazo[1,2-a][1,4]benzodiazepine;
8-fluoro-6-(2-pyrryl)-1,2-dimethyl-4H-imidazo[1,2-a][1,4]benzodiazepine;
8-nitro-6-(2-thienyl)-1,2-dimethyl-4H-imidazo[1,2-a][1,4]benzodiazepine;
8-trifluoromethyl-6-cyclohexyl-1,2-dimethyl-4H-imidazo[1,2-a][1,4]benzodiazepine;
8-cyano-6-(1-cyclohexenyl)-1,2-dimethyl-4H-imidazo[1,2-a][1,4]benzodiazepine;
8-methylthio-1,2,6-trimethyl-4H-imidazo[1,2-a][1,4]-benzodiazepine; and the like.

EXAMPLE 17

8-chloro-6-phenyl-4H-imidazo[1,2-a][1,4]benzodiazepine-1-carboxaldehyde (II)

A stirred solution of 6.0 g. (0.0194 mole) of 2-chloro-5-phenyl-2-(2-propynylamino)-3H-1,4-benzodiazepine (IV) in 20 ml. of acetic acid, 20 ml. of 88% formic acid and 1.5 ml. of water is treated at ambient temperature, dropwise, with 156 ml. of 5% aqueous solution of mercuric acetate. During the addition the temperature of the reaction mixture rises at aobut 35° C. The mixture is stirred at ambient temperature for about 3 hours and poured into ice water. This mixture is then extracted with chloroform. The extract thus obtained is washed with water and concentrated in vacuo. The residue is suspended in hot ethyl acetate and filtered. The filtrate is concentrated and chromatographed on 360 g. of silica gel with 50% ethyl acetate-Skellysolve B hexanes to give 960 mg. of 8-chloro-6-phenyl-4H-imidazo[1,2-a][1,4]benzodiazepine-1-carboxyldehyde as an amorphous solid.

Anal. Calcd. for $C_{18}H_{12}ClN_3O$: C, 67.19; H, 3.76; Cl, 11.02; N, 13.06. Found: C, 66.21; H, 4.03; Cl, 10.59; N, 11.59.

EXAMPLE 18

8-chloro-6-(2-chlorophenyl)-4H-imidazo[1,2-a][1,4]benzodiazepine-1-carboxaldehyde (II)

A stirred solution of 0.02 mole of 7-chloro-5-(2-chlorophenyl)-2-(2-propynylamino)-3H-1,4-benzodiazepine (IV), 20 ml. of acetic acid, 20 ml. of 88% formic acid and 1.5 ml. of water at ambient temperature is treated, dropwise, with 160 ml. of a 5% aqueous solution of mercuric acetate. The mixture is then stirred at room temperature for about 3 hours, poured into ice water and then extracted with chloroform. The extract thus obtained is washed with water and then concentrated in vacuo. The residue thus obtained is suspended in hot ethyl acetate and filtered. The filtrate is concentrated and chromatographed on silica gel with 50% ethyl acetate-hexanes to give 8-chloro-6-(2-chlorophenyl)-4H-imidazo[1,2-a][1,4]benzodiazepine-1-carboxaldehyde.

EXAMPLE 19

8-bromo-6-(2-pyridyl)-4H-imidazo[1,2-a][1,4]benzodiazepine-1-carboxaldehyde (II)

A stirred solution of 0.02 mole of 7-bromo-5-(2-pyridyl)-2-(2-propynylamino)-3H-1,4benzodiazepine (IV), 20 ml. of acetic acid, 20 ml. of 88% formic acid and 1.5 ml. of water at ambient temperature is treated, dropwise, with 160 ml. of a 5% aqueous solution of mercuric acetate. The mixture is then stirred at room temperature for about 3 hours, poured into ice water and then extracted with chloroform. The extract thus obtained is washed with water and then concentrated in vacuo. The residue thus obtained is suspended in hot ethyl acetate and filtered. The filtrate is concentrated and chromatographed on silica gel with 50% ethyl acetatehexanes to give 8-bromo-6-(2-pyridyl)-4H-imidazo[1,2-a][1,4]benzodiazepine-1-carboxaldehyde.

EXAMPLE 20

8-chloro-6-phenyl-2,4-dimethyl-4H-imidazo[1,2-a][1,4]benzodiazepine-1-carboxaldehyde (II)

A stirred solution of 0.02 mole of 7-chloro-3-methyl-5-phenyl-2-[(1-methyl-2-propynyl)amino]-3H-1,4benzodiazepine (IV), 20 ml. of acetic acid, 20 ml. of 88% formic acid and 1.5 ml of water at ambient temperature is treated, dropwise, with 160 ml. of a 5% aqueous solution of mercuric acetate. The mixture is then stirred at room temperature for about 3 hours, poured into ice water and then extracted with chloroform. The extract thus obtained is washed with water and then concentrated in vacuo. The residue thus obtained is suspended in hot ethyl acetate and filtered. The filtrate is concentrated and chromatographed on silica gel with 50% ethyl acetate-hexanes to give 8-chloro-6-phenyl-2,4-dimethyl-4H-imidazo[1,2-a][1,4]benzodiazepine-1-carboxaldehyde.

EXAMPLE 21

8-chloro-6-(2-chlorophenyl)-2-methyl-4H-imidazo[1,2-a][1,4]benzodiazepine-1-carboxaldehyde (II)

A stirred solution of 0.02 mole of 7-chloro-5-(2-chlorophenyl)-2-[(1-methyl-2-propynyl)amino]-3H-1,4benzodiazepine (IV), 20 ml. of acetic acid, 20 ml. of 88% formic acid and 1.5 ml. of water at ambient temperature is treated, dropwise, with 160 ml. of a 5% aqueous solution of mercuric acetate. The mixture is then stirred at room temperature for about 3 hours, poured into ice water and then extracted with chloroform. The extract thus obtained is washed with water and then concentrated in vacuo. The residue thus obtained is suspended in hot ethyl acetate and filtered. The filtrate is concentrated and chromatographed on silica gel with 50% ethyl acetate-hexanes to give 8-chloro-6-(2-chlorophenyl)-2-methyl-4H-imidazo[1,2-a][1,4]benzodiazepine-1-carboxaldehyde.

In the manner given in Examples 17–21, above, other 2-(2-propynylamino) and (1-alkyl-2-propynylamino)-3H-1,4benzodiazepines of formula (IV), for example those prepared and listed in Example 8, above, can be subjected to ring closure to obtain the corresponding 4H-imidazo[1,2-a][1,4]benzodiazepine-1-carboxaldehydes of formula (II), respectively, such as 8-bromo-6-phenyl-4H-imidazo[1,2-a][1,4]benzodiazepine-1-carboxaldehyde;
8-fluoro-6-phenyl-4H-imidazo[1,2-a][1,4]benzodiazepine-1-carboxaldehyde;
9-nitro-6-phenyl-4H-imidazo[1,2-a][1,4]benzodiazepine-1-carboxaldehyde;
8-trifluoromethyl-6-phenyl-4H-imidazo[1,2-a][1,4]benzodiazepine-1-carboxaldehyde;
8-cyano-6-phenyl-4H-imidazo[1,2-a][1,4]benzodiazepine-1-carboxaldehyde;
8-methylthio-6-phenyl-4H-imidazo[1,2-a][1,4]benzodiazepine-1-carboxaldehyde;
8-bromo-6-(2-chlorophenyl)-4H-imidazo[1,2-a][1,4]benzodiazepine-1-carboxaldehyde;
8-fluoro-6-(2-chlorophenyl)-4H-imidazo[1,2-a][1,4]benzodiazepine-1-carboxaldehyde;
8-nitro-6-(2-chlorophenyl)-4 H-imidazo[1,2-a][1,4]benzediazepine-1-carboxaldehyde;
8-trifluoromethyl-6-(2-chlorophenyl)-4H-imidazo[1,2-a][1,4]benzodiazepine-1-carboxaldehyde;
8-cyano-6-(2-chlorophenyl)-4H-imidazo[1,2-a][1,4]benzodiazepine-1-carboxaldehyde;
8-methylthio-6-(2-chlorophenyl)-4H-imidazo[1,2-a][1,4]benzodiazepine-1-carboxaldehyde;
8-chloro-6-(2-fluorophenyl)-4H-imidazo[1,2-a][1,4]benzodiazepine-1-carboxaldehyde;
8-bromo-6-(2-fluorophenyl)-4H-imidazo[1,2-a][1,4]benzodiazepine-1-carboxaldehyde;
8-fluoro-6-(2-fluorophenyl)-4H-imidazo[1,2-a][1,4]benzodiazepine-1-carboxaldehyde;
8-nitro-6-(2-fluorophenyl)-4H-imidazo[1,2-a][1,4]benzodiazepine-1-carboxaldehyde;
8-trifluoromethyl-6-(2-fluorophenyl)-4H-imidazo[1,2-a][1,4]benzodiazepine-1-carboxaldehyde;
8-cyano-6-(2-fluorophenyl)-4H-imidazo[1,2-a][1,4]benzodiazepine-1-carboxaldehyde;
8-methylthio-6-(2-fluorophenyl)-4H-imidazo[1,2-a][1,4benzodiazepine-1-carboxaldehyde;
8-chloro-6-(2-pyrimidyl)-4H-imidazo[1,2-a][1,4]benzodiazepine-1-carboxaldehyde;
8-bromo-6-(2-furyl)-4H-imidazo[1,2-a][1,4]benzodiazepine-1-carboxaldehyde;
8-fluoro-6-(2-pyrryl)-4H-imidazo[1,2-a][1,4]benzodiazepine-1-carboxaldehyde;
8-nitro-6-(2-thienyl)-4H-imidazo[1,2-a][1,4]benzodiazepine-1-carboxaldehyde;
8-trifluoromethyl-6-cyclohexyl-4H-imidazo[1,2-a]1,4]benzodiazepine-1-carboxaldehyde;
8-cyano-6-(1-cyclohexenyl)-4H-imidazo[1,2-a][1,4]benzodiazepine-1-carboxaldehyde;

8-methylthio-6-methyl-4H-imidazo[1,2-a][1,4]benzodiazepine-1-carboxaldehyde;
8-bromo-6-phenyl-2-methyl-4H-imidazo[1,2-a][1,4]benzodiazepine-1-carboxaldehyde;
8-fluoro-6-phenyl-2-methyl-4H-imidazo[1,2-a][1,4-benzodiazepine-1-carboxaldehyde;
8-nitro-6-phenyl-2-methyl-4H-imidazo[1,2-a][1,4]benzodiazepine-1-carboxaldehyde;
8-trifluoromethyl-6-phenyl-2-methyl-4H-imidazo[1,2-a][1,4]benzodiazepine-1-carboxaldehyde;
8-cyano-6-phenyl-2-methyl-4H-imidazo[1,2-a][1,4]benzodiazepine-1-carboxaldehyde;
8-methylthio-6-phenyl-2-methyl-4H-imidazo[1,2-a][1,4]benzodiazepine-1-carboxaldehyde;
8-bromo-6-(2-chlorophenyl)-2-methyl-4H-imidazo[1,2-a][1,4]benzodiazepine-1-carboxaldehyde;
8-fluoro-6-(2-chlorophenyl)-2-methyl-4H-imidazo[1,2-a][1,4]benzodiazepine-1-carboxaldehyde;
8-nitro-6-(2-chlorphenyl)-2-methyl-4H-imidazo[1,2-a][1,4]benzodiazepine-1-carboxaldehyde;
8-trifluoromethyl-6-(2-chlorophenyl)-2-methyl-4H-imidazo[1,2-a][1,4]benzodiazepine-1-carboxaldehyde;
8-cyano-6-(2-chlorophenyl)-2-methyl-4H-imidazo[1,2-a][1,4]benzodiazepine-1-carboxaldehyde;
8-methylthio-6-(2-chlorophenyl)-2-methyl-4H-imidazo[1,2-a][1,4]benzodiazepine-1-carboxaldehyde;
8-chloro-6-(2-fluorophenyl)-2-methyl-4H-imidazo[1,2-a][1,4]benzodizepine-1-carboxaldehyde;
8-bromo-6-(2-fluorophenyl)-2-methyl-4H-imidazo[1,2-a][1,4]benzodiazepine-1-carboxaldehyde;
8-fluoro-6-(2-fluorophenyl)-2-methyl-4H-imidazo[1,2-a][1,4]benzodiazepine1 1-carboxaldehyde;
8-nitro-6-(2-fluorophenyl)-2-methyl-4H-imidazo[1,2-a][1,4]benzodiazepine-1-carboxaldehyde;
8-trifluoromethyl-6-(2-fluorophenyl)-2-methy-4H-imidazo[1,2-a][1,4]benzodiazepine-1-carboxaldehyde;
8-cyano-6-(2-fluorophenyl)-2-methyl-4H-imidazo[1,2-a][1,4]benzodiazepine-1-carboxaldehyde
8-methylthio-6-(2-flurophenyl)-2-methyl-4H-imidazo[1,2-a][1,4]benzodiazepine-1-carboxaldehyde;
8-chloro-6-(2-pyrimidyl)-2-methyl-4H-imidazo[1,2-a][1,4]benzodiazepine-1-carboxaldehyde;
8-bromo-6-(2-furyl)-2-methyl-4H-imidazo[1,2-a][1,4]benzodiazepine-1-carboxaldehyde;
8-fluoro-6-(2-pyrryl)-2-methyl-4H-imidazo[1,2-a][1,4]benzodiazepine-1-carboxaldehyde;
8-nitro-6-(2-thienyl)-2-methyl-4H-imidazo[1,2-a][1,4]benzodiazepine-1-carboxaldehyde;
8-trifluoromethyl-6-cyclohexyl-2-methyl-4H-imidazo[1,2-a][1,4]benzodiazepine-1-carboxaldehyde;
8-cyano-6-(1-cyclohexenyl)-2-methyl-4H-imidazo[1,2-a][1,4]benzodiazepine-1-carboxaldehyde;
8-methylthio-2,6-dimethyl-4H-imidazo[1,2-a][1,4]benzodiazepine-1-carboxaldehyde; and the like.

EXAMPLE 22

8-chloro-6-phenyl-4H-imidazo[1,2-a][1,4]benzodiazepine (Ia)

A mixture of 1.0 g. of 8-chloro-6-phenyl-4H-imidazo-[1,2-a][1,4]benzodiazepine-1-carboxaldehyde (II) and 0.1 g. of tris(triphenylphosphine)rhodium chloride in 50 ml. of benzene is refluxed for about 6 hours. The mixture is then allowed to cool and filtered to remove the catalyst. The filtrate thus obtained in concentrated in vacuo to give 8-chloro-6-phenyl-4H-imidazo[1,2-a][1,4]benzodiazepine, which is further purified by chromatography on silica gel and/or crystallization, m.p. 146°–148° C.

Anal. Calcd. for $C_{17}H_{12}ClN_3$: C, 69.50; H, 4.12; Cl, 12.07; N, 14.31. Found: C, 69.32; H, 4.04; Cl, 12.08; N, 14.51.

EXAMPLE 23

8-chloro-6-(2-chlorophenyl)-4H-imidazo[1,2-a]-[1,4]benzodiazepine (Ia)

A mixture of 1.0 g. of 8-chloro-6-(2-chlorophenyl)-4H-imidazo[1,2-a][1,4]benzodiazepine-1-carboxaldehyde (II) and 0.1 g. of tris(triphenylphosphine)rhodium chloride in 50 ml. of benzene is refluxed for about 6 hours. The mixture is then allowed to cool and filtered to remove the catalyst. The fitrate thus obtained is concentrated in vacuo to give 8-chloro-6-(2-chlorophenyl)-4H-imidazo[1,2-a][1,4]benzodiazepine, which is further purified by chromatography on silica gel and/or crystallization, m.p. 179°–180° C.

Anal. Calc. for $C_{17}H_{11}Cl_2N_3$: C, 62.21; H, 3.38; Cl, 21.60; N, 12.81. Found: c, 61.98; H, 3.27; Cl, 21.72; N, 13.08.

EXAMPLE 24

8-chloro-6-(2-pyridyl)-4-imidazo[1,2-a][1,4]benzodiazepine (Ia)

A mixture of 1.0 of 8-chloro-6-(2-pyridyl)-4-H-imidazo-[1,2-a][1,4]benzodiazepine-1-carboxaldehyde (II) and 0.1 g. of tris(triphenylphosphine)rhodium chloride in 50 ml. of benzene is refluxed for about 6 hours. The mixture is then allowed to cool and filtered to remove the catalyst. The filtrate thus obtained is concentrated in vacuo to give 8-chloro-6-(2-pyridyl)-4H-imidazo[1,2-a][1,4]benzodiazepine, which is further purified by chromatography on silica gel and/or crystallization.

EXAMPLE 25

8-chloro-6-phenyl-2,4-dimethyl-4H-imidazo[1,2-a][1,4]benzodiazepine (Ia)

A mixture of 1.0 g. of 8-chloro-6-phenyl-2,4-dimethyl-4H-imidazo[1,2-a][1,4]benzodiazepine-1-carboxaldehyde (II) and 0.1 g. of tris(triphenylphosphine)rhodium chloride in 50 ml. of benzene is refluxed for about 6 hours. The mixture is then allowed to cool and filtered to remove the catalyst. The filtrate thus obtained is concentrated in vacuo to give 8-chloro-6-phenyl-2,4-dimethyl-4H-imidazo[1,2-a][1,4-benzodiazepine, which is further purified by chromatography and/or crystallization.

EXAMPLE 26

8-chloro-6-(2-chlorophenyl)-2-methyl-4H-imidazo[1,2-a][1,4]benzodiazepine (Ia)

A mixture of 1.0 g. of 8-chloro-6-(2-chlorophenyl)-2-methyl-4H-imidazo[1,2-a][1,4]benzodiazepine-1-carboxaldehyde (II) and 0.1 g. of tris(triphenylphosphine)rhodium chloride in 50 ml. of benzene is refluxed for about 6 hours. The mixture is then allowed to cool and filtered to remove the catalyst. The filtrate thus obtained is concentrated in vacuo to give 8-chloro-6-(2-chlorophenyl)-2-methyl-4H-imidazo[1,2-a][1,4]benzodiazepine, which is further purified by chromatography on silica gel and/or crystallization.

In the manner given in Examples 22–26, above, other 4H-imidazo[1,2-a][1,4]benzodiazepine-1-carboxaldehydes of formula II, for example those prepared and listed in Example 21, above, can be treated with tris (triphenylphosphine(rhodium chloride to obtain the corresponding compounds (Ia) which are unsubstituted at the 1-position, such as:

8-bromo-6-phenyl-4H-imidazo[1,2-a][1,4]benzodiazepine;
8-fluoro-6-phenyl-4H-imidazo[1,2-a][1,4]benzodiazepine;
8-nitro-6-phenyl-4H-imidazo[1,2-a][1,4]benzodiazepine;
8-trifluoromethyl-6-phenyl-4H-imidazo[1,2-a][1,4]benzodiazepine;
8-cyano-6-phenyl-4H-imidazo[1,2-a][1,4]benzodiazepine;
8-methylthio-6-phenyl-4H-imidazo[1,2-a][1,4-benzodiazepine;
8-bromo-6-(2-chlorophenyl)-4H-imidazo[1,2-a][1,4]benzodiazepine;
8-fluoro-6-(2-chlorophenyl)-4H-imidazo[1,2-a][1,4]benzodiazepine;
8-nitro-6-(2-chlorophenyl)-4H-imidazo[1,2-a][1,4]benzodiazepine;
8-trifluoromethyl-6-(2-chlorophenyl)-4H-imidazo[1,2-a][1,4benzodiazepine;
8-cyano-6-(2-chlorophenyl)-4H-imidazo[1,2-a][1,4]benzodiazepine;
8-methylthio6-(2chlorophenyl)-4H-imidazo[1,2-a][1,4]benzodiazepine;
8-chloro-6-(2-fluorophenyl)-4H-imidazo[1,2-a][1,4]benzodiazepine;
8-bromo-6-(2-fluorophenyl)-4H-imidazo[1,2-a][1,4]benzodiazepine;
8-fluoro-6-(2-fluorophenyl)-4H-imidazo[1,2-a][1,4]benzodiazepine;
8-nitro-6-(2-fluorophenyl)-4H-imidazo[1,2-a][1,4]benzodiazepine;
8-trifluoromethyl-6-(2-fluorophenyl-4H-imidazo[1,2-a]-[1,4]benzodiazepine;
8-cyano-6-(2-fluorophenyl)-4H-imidazo[1,2-a][1,4]benzodiazepine;
8-methylthio-6-(2-fluorophenyl)-4H-imidazo[1,2-a][1,4]benzodiazepine;
8-chloro-6-(2-pyrimidyl)-4H-imidazo[1,2-a][1,4]benzodiazepine;
8-bromo-6-(2-furyl)-4H-imidazo[1,2-a][1,4]benzodiazepine
8-fluoro-6-(2-pyrryl)-4H-imidazo[1,2-a][1,4]benzodiazepine;
8-nitro-6-(2-thienyl)-4H-imidazo[1,2-a][1,4]benzodiazepine;
8-trifluoromethyl-6-cyclohexyl-4H-imidazo[1,2-a][1,4]benzodiazepine;
8-cyano-6-(1-cyclohexenyl)-4H-imidazo[1,2-a][1,4]benzodiazepine;
8-methylthio-6-methyl-4H-imidazo[1,2-a][1,4]benzodiazepine;
8-bromo-6-phenyl-2-methyl-4H-imidazo[1,2a][1,4-]benzodiazepine;
8-fluoro-6-phenyl-2-methyl-4H-imidazo[1,2-a][1,4]benzodiazepine;
8-nitro-6-phenyl-2-methyl-4H-imidazo[1,2-a][1,4]benzodiazepine;
8-trifluoromethyl-6-phenyl-2-methyl-4H-imidazo[1,2-a][1,4]benzodiazepine;
8-cyano-6-phenyl-2-methyl-4H-imidazo[1,2-a][1,4]benzodiazepine;
8-methylthio-6-phenyl-2-methyl-4H-imidazo[1,2-a][1,4]benzodiazepine;
8-bromo-6-(2-chlorophenyl)-2-methyl-4H-imidazo[1,2-a][1,4]benzodiazepine;
8-fluoro-6-(2-chlorophenyl)-2-methyl-4H-imidazo[1,2-a][1,4]benzodiazepine;
8-nitro-6-(2-chlorophenyl)-2-methyl-4H-imidazo[1,2-a][1,4]benzodiazepine;
8-trifluoromethyl-6-(2-chlorophenyl)-2-methyl-4H-imidazo-[1,2-a][1,4]benzodiazepine;
8-cyano-6-(2-chlorophenyl)-2-methyl-4H-imidazo[1,2-a][1,4]benzodiazepine.
8-methylthio-6-(2-chlorophenyl)-2-methyl-4H-imidazo[1,2-a][1,4]benzodiazepine;
8-chloro-6-(2-fluorophenyl)-2-methyl-4H-imidazo[1,2-a][1,4]benzodiazepine;
8-bromo-6-(2-fluorophenyl)-2-methyl-4H-imidazo[1,2-a][1,4]benzodiazepine;
8-fluoro-6-(2-fluorophenyl)-2-methyl-4H-imidazo[1,2-a][1,4]benzodiazepine;
8-nitro-6-(2-fluorophenyl)-2-methyl-4H-imidazo[1,2-a][1,4]benzodiazepine;
8-trifluoromethyl-6-(2-fluorophenyl)-2-methyl-4H-imidazo[1,2-a][1,4]benzodiazepine;
8-cyano-6-(2-fluorophenyl)-2-methyl-4H-imidazo[1,2-a][1,4]benzodiazepine;
8-methylthio-6-(2-fluorophenyl)-2-methyl-4H-imidazo[1,2-a][1,4]benzodiazepine;
8-chloro-6(2-pyrimidyl)-2-methyl-4H-imidazo[1,2-a][1,4]benzodiazepine;
8-bromo- 6-(2-furyl)-2-methyl-4H-imidazo[1,2-a][1,4]benzodiazepine;
8-fluoro-6-(2-pyrryl)-2methyl-4H-imidazo[1,2-a][1,4]-benzodiazepine;
8-nitro-6-(2-thienyl)-2-methyl-4H-imidazo[1,2-a][1,4]-benzodiazepine;
8-trifluoromethyl-6-cyclohexeyl-2-methyl-4H-imidazo[1,2-a][1,4]benzodiazepine;
8-cyano-6-(1-cyclohexenyl)-2-methyl-4H-imidazo[1,2-a][1,4]benzodiazepine;
8-methylthio-2,6-dimethyl-4H-imidazo[1,2-a][1,4]benzodiazepine; and the like.

EXAMPLE 27

8-chloro-1-methyl-6-phenyl-4H-imidazo[1,2-a][1,4]benzodiazepin-5-oxide (III)

A stirred solution of 1.0 g. of 8-chloro-1-methyl-6-phenyl-4H-imidazo[1,2-a][1,4]benzodiazepine (Ia) in absolute ethanol in an ice bath is treated with 1.0 g. of m-chloroperbenzoic acid. The mixture is allowed to stand in the ice bath for about 8 hous and at room temperature at about 24° C. for approximately 18 hours. It is then concentrated in vacuo, the residue thus obtained is suspended in aqueous, cold, dilute potassium carbonate solution and extracted with methylene chloride. The extract is washed with water, dried and concentrated in vacuo. The residue thus obtained is chromatographed on 100 g. of silica gel to give 8-chloro-1-methyl-6-phenyl-4H-imidazo[1,2-a][1,4]benzodiazepine-5-oxide.

EXAMPLE 28

8-chloro-6-(2-chlorophenyl)-1-methyl-4H-imidazo[1,2-a][1,4]benzodiazepine-5-oxide (III)

A stirred mixture is 1.0 g. of 8-chloro-6-(2-chlorophenyl)-1-methyl-4H-imidazo[1,2-a][1,4]benzodiazepine (Ia) in absolute ethanol in an ice bath is treated with 1.0 g. of m-chloroperbenzoic acid. The mixture is allowed to stand in the ice bath for about 8 hours at room temperature at about 24°C. for approximately 18 hours. It is then concentrated in vacuo, the residue thus obtained is suspended in aqueous, cold, dilute potassium carbonate solution and extracted with methylene chloride. The extract is washed with water, dried and concentrated in vacuo. The residue thus obtained is chromatographed on 100 g. of silica gel to give 8-chloro-6-(2-chlorophenyl)-1-methyl-4H-imidazo[1,2-a][1,4]benzodiazepine-5-oxide In the same manner following the procedure of Examples 27 and 28, above, the other 4H-imidazo[1,2-a][1,4]benzodiazepines of formula Ia, for example, those prepared in Examples 11–16 and 22 through 25, above, can likewise be converted to the corresponding 5-oxides (III). The following are representative:

8-chloro-6-(2,6-difluorophenyl)-1-ethyl-4H-imidazo[1,2-a][1,4]benzodiazepine to obtain 8-chloro-6-(2,6-difluorophenyl)-1-ethyl-4H-imidazo[1,2-a][1,4]benzodiazepine-5-oxide;

8-trifluoromethyl-6-phenyl-1-propyl-4H-imidazo[1,2-a][1,4]benzodiazepine to obtain 8-trifluoromethyl-6-phenyl-1-propyl-4H-imidazo[1,2-a][1,4]benzodiazepine-5-oxide;

8-bromo-1-methyl-6-(2-pyridyl)-4H-imidazo[1,2-a][1,4]benzodiazepine to obtain 8-bromo-1-methyl-6-(2-pyridyl)-4H-imidazo[1,2-a][1,4]benzodiazepine-5oxide;

8-chloro-2,6-dimethyl-1-propyl-4H-imidazo[1,2-a][1,4]benzodiazepine to obtain 8-chloro-2,6-dimethyl-1-propyl-4H-imidazo[1,2-a][1,4]benzodiazepine-5-oxide;

8-chloro-1,2,4-trimethyl-6-phenyl-4H-imidazo[1,2-a][1,4]benzodiazepine to obtain 8-chloro-1,2,4-trimethyl-6-phenyl-4H-imidazo[1,2-a][1,4]benzodiazepine-5-oxide;

8-chloro-1,2-dimethyl-6-(2-chlorophenyl)-4H-imidazo[1,2-a][1,4]benzodiazepine to obtain 8-chloro-1,2-dimethyl-6-(2-chlorophenyl)-4H-imidazo[1,2-a][1,4]benzodiazepine-5-oxide;

8-chloro-6-phenyl-4H-imidazo[1,2-a][1,4]benzodiazepine to obtain 8-chloro-6-phenyl-4H-imidazo[1,2-a][1,4]benzodiazepine-5-oxide;

8-chloro-6-(2-chlorophenyl)-4H-imidazo[1,2-a][1,4]benzodiazepine to obtain 8-chloro-6-(2-chlorophenyl)-4H-imidazo[1,2-a][1,4]benzodiazepine-5-oxide;

8-chloro-6-(2-pyridyl)-4H-imidazo[1,2-a][1,4]benzodiazepine to obtain 8-chloro-6-(2-pyridyl)-4H-imidazo[1,2-a][1,4]benzodiazepine-5-oxide;

8-chloro-2,4-dimethyl-6-phenyl-4H-imidazo[1,2-a][1,4]benzodiazepine to obtain 8-chloro-2,4-dimethyl-6-phenyl-4H-imidazo[1,2-a][1,4]benzodiazepine-5-oxide; and 8-chloro-6-(2-chlorophenyl)-2-methyl-4H-imidazo[1,2-a][1,4]benzodiazepine to obtain 8-chloro-6-(2-chlorophenyl)-2-methyl-4H-imidazo[1,2-a][1,4]benzodiazepine to obtain 8-chloro-6-(2-chlorophenyl)-2methyl-[4H-imidazo[1,2-a][1,4]benzodiazepine-5-oxide.
methyl-[4H-imidazo[1,2,-a]

Similarly, following the procedure of Examples 27 and 28, the other compounds of formula Ia can likewise be converted to the corresponding 5-oxides (III), for example the compounds listed in Examples 16 and 26, above, give:

8-bromo-6-phenyl-1-methyl-4H-imidazo[1,2-a][1,4]benzodiazepine-5-oxide;

8-fluoro-6-phenyl-1-methyl-4H-imidazo[1,2-a][1,4]benzodiazepine-5-oxide;

8-nitro-6-phenyl-1-methyl-4H-imidazo[1,2-a][1,4]benzodiazepine-5-oxide;

8-trifluoromethyl-6-phenyl-1-methyl-4H-imidazo[1,2-a][1,4]benzodiazepine-5-oxide;

8-cyano-6-phenyl-1-methyl-4H-imidazo[1,2-a][1,4]benzodiazepine-5-oxide;

8-methylthio-6-phenyl-1-methyl-4H-imidazo[1,2-a][1,4]benzodiazepine-5-oxide;

8-bromo-6-(2-chlorophenyl)-1-methyl-4H-imidazp[1,2-a][1,4]benzodiazepine-5-oxide;

8-fluoro-6-(2-chlorophenyl)-1-methyl-4H-imidazo[1,2-a][1,4]benzodiazepine-5-oxide;

8-nitro-6-(2-chlorophenyl)-1-methyl-4H-imidazo[1,2-a][1,4]benzodiazepine-5-oxide;

8-trifluoromethyl-6-(2-chlorophenyl)-1-methyl-4H-imidazo[1,2-a][1,4]benzodiazepine-5-oxide;

8-cyano-6-(2-chlorophenyl)-1-methyl-4H-imidazo[1,2-a][1,4]benzodiazepine-5-oxide;

8-methylthio-6-(2-chlorophenyl)-1-methyl-4H-imidazo[1,2-a][1,4]benzodiazepine-5-oxide;

8-chloro-6-(2-fluorophenyl)-1-methyl-4H-imidazo[1,2-a][1,4]benzodiazepine-5-oxide;

8-bromo-6-(2-fluorophenyl)-1-methyl-4H-imidazo[1,2-a][1,4]benzodiazepine-5-oxide;

8-fluoro-6-(2-fluorophenyl)-1-methyl-4H-imidazo[1,2-a][1,4]benzodiazepine-5-oxide;

8-nitro-6-(2-fluorophenyl)-1-methyl-4H-imidazo[1,2-a][1,4]benzodiazepine-5-oxide;

8-trifluoromethyl-6-(2-fluorophenyl)-1-methyl-4H-imidazo[1,2-a][1,4]benzodiazepine-5-oxide;

8-cyano-6-(2-fluorophenyl)-1-methyl-4H-imidazo[1,2-a][1,4]benzodiazepine-5-oxide;

8-methylthio-6-(2-fluorophenyl)-1-methyl-4H-imidazo[1,2-a][1,4]benzodiazepine-5-oxide;

8-chloro-6-(2-pyrimidyl)-1-methyl-4-H-imidazo[1,2-a][1,4]benzodiazepine-5-oxide;

8-bromo-6-(2-furyl)-1-methyl-4H-imidazo[1,2-a][1,4]benzodiazepine-5-oxide;

8-fluoro-6-(2-pyrryl)-1-methyl-4H-imidazo[1,2-a][1,4]benzodiazepine-5-oxide;

8-nitro-6-(2-thienyl)-1-methyl-4H-imidazo[1,2-a][1,4]benzodiazepine-5-oxide;

8-trifluoromethyl-6-cyclohexyl-1-methyl-4H-imidazo[1,2-a][1,4]benzodiazepine-5-oxide;

8-cyano-6-(1-cyclohexenyl)-1-methyl-4H-imidazo[1,2-a][1,4]benzodiazepine-5-oxide;

8-methylthio-1,6-dimethyl-4H-imidazo[1,2-a][1,4]benzodiazepine-5-oxide;

8-bromo-6-phenyl-1,2-dimethyl-4H-imidazo[1,2-a][1,4]benzodiazepine-5-oxide;
8-fluoro-6-phenyl-1,2-dimethyl-4-H-imidazo[1,2-a][1,4]benzodiazepine-5-oxide;
8-nitro-6-phenyl-1,2-dimethyl-4H-imidazo[1,2-a][1,4]benzodiazepine-5-oxide;
8-trifluoromethyl-6-phenyl-1,2-dimethyl-4H-imidazo[1,2-a][1,4]benzodiazepine-5-oxide;
8-cyano-6-phenyl-1,2-dimethyl-4H-imidazo[1,2-a][1,4]benzodiazepine-5-oxide;
8-methylthio-6-phenyl-1,2-dimethyl-4H-imidazo[1,2-a][1,4]benzodiazepine-5-oxide;
8-bromo-6-(2-chlorophenyl)-1,2-dimethyl-4H-imidazo[1,2-a][1,4]benzodiazepine-5-oxide;
8-fluoro-6-(2-chlorophenyl)-1,2-dimethyl-4H-imidazo[1,2-a][1,4]benzodiazepine-5-oxide;
8-nitro-6-(2-chlorophenyl)-1,2-dimethyl-4H-imidazo[1,2-a][1,4]benzodiazepine-5-oxide;
8-trifluoromethyl-6-(2-chlorophenyl)-1,2-dimethyl-4H-imidazo[1,2-a][1,4]benzodiazepine-5-oxide;
8-cyano-6-(2-chlorophenyl)-1,2-dimethyl-4H-imidazo[1,2-a][1,4]benzodiazepine-5-oxide;
8-methylthio-6-(2-chlorophenyl)-1,2-dimethyl-4H-imidazo[1,2-a][1,4]benzodiazepine-5-oxide;
8-chloro-6-(2-fluorophenyl)-1,2-dimethyl-4H-imidazo[1,2-a][1,4]benzodiazepine-5-oxide;
8-bromo-6-(2-fluorophenyl)-1,2-dimethyl-4H-imidazo[1,2-a][1,4]benzodiazepine-5-oxide;
8-fluoro-6-(2-fluorophenyl)-1,2-dimethyl-4H-imidazo[1,2-a][1,4]benzodiazepine-5-oxide;
8-nitro-6-(2-fluorophenyl)-1,2-dimethyl-4H-imidazo[1,2-a][1,4]benzodiazepine-5-oxide;
8-trifluoromethyl-6-(2-fluorophenyl)-1,2-dimethyl-4H-imidazo[1,2-a][1,4]benzodiazepine-5-oxide;
8-cyano-6-(2-fluorophenyl)-1,2-dimethyl-4H-imidazo[1,2-a][1,4]benzodiazepine-5-oxide;
8-methylthio-6-(2-fluorophenyl)-1,2-dimethyl-4H-imidazo[1,2-a][1,4]benzodiazepine-5-oxide;
8-chloro-6-(2-pyrimidyl)-1,2-dimethyl-4H-imidazo[1,2-a][1,4]benzodiazepine-5-oxide;
8-bromo-6-(2-furyl)-1,2-dimethyl-4H-imidazo[1,2-a][1,4]benzodiazepine-5-oxide;
8-fluoro-6-(2-pyrryl)-1,2-dimethyl-4H-imidazo[1,2-a][1,4]benzodiazepine-5-oxide;
8-nitro-6-(2-thienyl)-1,2-dimethyl-4H-imidazo[1,2-a][1,4]benzodiazepine-5-oxide;
8-trifluoromethyl-6-cyclohexyl-1,2-dimethyl-4H-imidazo[1,2-a][1,4]benzodiazepine-5-oxide;
8-cyano-6-(1-cyclohexenyl)-1,2-dimethyl-4H-imidazo[1,2-a][1,4]benzodiazepine-5-oxide;
8-methylthio-6-methyl-1,2-dimethyl-4H-imidazo[1,2-a][1,4]benzodiazepine-5-oxide;
8-bromo-6-phenyl-4H-imidazo[1,2-a][1,4]benzodiazepine-5-oxide;
8-fluoro-6-phenyl-4H-imidazo[1,2-a][1,4]benzodiazepine-5-oxide;
8-nitro-6-phenyl-4H-imidazo[1,2-a][1,4]benzodiazepine-5-oxide;
8-trifluoromethyl-6-phenyl-4H-imidazo[1,2-a][1,4]benzodiazepine-5-oxide;
8-cyano-6-phenyl-4H-imidazo[1,2-a][1,4]benzodiazepine-5-oxide;
8-methylthio-6-phenyl-4H-imidazo[1,2-a][1,4]benzodiazepine-5-oxide;
8-bromo-6-(2-chlorophenyl)-4H-imidazo[1,2-a][1,4]benzodiazepine-5-oxide;
8-fluoro-6-(2-chlorophenyl)-4H-imidazo[1,2-a][1,4]benzodiazepine-5-oxide;
8-nitro-6-(2-chlorophenyl)-4H-imidazo[1,2-a][1,4]benzodiazepine-5-oxide;
8-trifluoromethyl-6-(2-chlorophenyl)-4H-imidazo[1,2-a][1,4]benzodiazepine-5-oxide;
8-cyano-6-(2-chlorophenyl)-4H-imidazo[1,2-a][1,4]benzodiazepine-5-oxide;
8-methylthio-6-(2-chlorophenyl)-4H-imidazo[1,2-a][1,4]benzodiazepine-5-oxide;
8-chloro-6-(2-fluorophenyl)-4H-imidazo[1,2-a][1,4]benzodiazepine-5-oxide;
8-bromo-6-(2-fluorophenyl)-4H-imidazo[1,2-a][1,4]benzodiazepine-5-oxide;
8-fluoro-6-(2-fluorophenyl)-4H-imidazo[1,2-a][1,4]benzodiazepine-5-oxide;
8-nitro-6-(2-fluorophenyl)-4H-imidazo[1,2-a][1,4]benzodiazepine-5-oxide;
8-trifluoromethyl-6-(2-fluorophenyl)-4H-imidazo[1,2-a][1,4]benzodiazepine-5-oxide;
8-cyano-6-(2-fluorophenyl)-4H-imidazo[1,2-a][1,4]benzodiazepine-5-oxide;
8-methylthio-6-(2-fluorophenyl)-4H-imidazo[1,2-a][1,4]benzodiazepine-5-oxide;
8-chloro-6-(2-pyrimidyl)-4H-imidazo[1,2-a][1,4]benzodiazepine-5-oxide;
8-bromo-6-(2-furyl)-4H-imidazo[1,2-a][1,4]benzodiazepine-5-oxide;
8-fluoro-6-(2-pyrryl)-4H-imidazo[1,2-a][1,4]benzodiazepine-5-oxide;
8-nitro-6-(2-thienyl)-4H-imidazo[1,2-a][1,4]benzodiazepine-5-oxide;
8-trifluoromethyl-6-cyclohexyl-4H-imidazo[1,2-a][1,4]benzodiazepine-5-oxide;
8-cyano-6-(1-cyclohexenyl)-4H-imidazo[1,2-a][1,4]benzodiazepine-5-oxide;
8-methylthio-6-methyl-4H-imidazo[1,2-a][1,4]benzodiazepine-5-oxide;
8-bromo-6-phenyl-2-methyl-4H-imidazo[1,2-a][1,4]benzodiazepine-5-oxide;
8-fluoro-6-phenyl-2-methyl-4H-imidazo[1,2-a][1,4]benzodiazepine-5-oxide;
8-nitro-6-phenyl-2-methyl-4H-imidazo[1,2-a][1,4]benzodiazepine-5-oxide;
8-trifluoromethyl-6-phenyl-2-methyl-4H-imidazo[1,2-a][1,4]benzodiazepine-5-oxide;
8-cyano-6-phenyl-2-methyl-4H-imidazo[1,2-a][1,4]benzodiazepine-5-oxide;
8-methylthio-6-phenyl-2-methyl-4H-imidazo[1,2-a][1,4]benzodiazepine-5-oxide;
8-bromo-6-(2-chlorophenyl)-2-methyl-4H-imidazo[1,2-a][1,4]benzodiazepine-5-oxide;
8-fluoro-6-(2-chlorophenyl)-2-methyl-4H-imidazo[1,2-a][1,4]benzodiazepine-5-oxide;
8-nitro-6-(2-chlorophenyl)-2-methyl-4H-imidazo[1,2-a][1,4]benzodiazepine-5-oxide;
8-trifluoromethyl-6-(2-chlorophenyl)-2-methyl-4H-imidazo[1,2-a][1,4]benzodiazepine-5-oxide;
8-cyano-6-(2-chlorophenyl)-2-methyl-4H-imidazo[1,2-a][1,4]benzodiazepine-5-oxide;
8-methylthio-6-(2-chlorophenyl)-2-methyl-4H-imidazo-[1,2-a][1,4]benzodiazepine-5-oxide;
8-chloro-6-(2-fluorophenyl)-2-methyl-4H-imidazo[1,2-a][1,4]benzodiazepine-5-oxide;
8-bromo-6-(2-fluorophenyl)-2-methyl-4H-imidazo[1,2-a]-[1,4]benzodiazepine-5-oxide;
8-fluoro-6-(2-fluorophenyl)-2-methyl-4H-imidazo[1,2-a][1,4]benzodiazepine-5-oxide;
8-nitro-6-(2-fluorophenyl)-2-methyl-4H-imidazo[1,2-a][1,4]benzodiazepine-5-oxide;

8-trifluoromethyl-6-(2-fluorophenyl)-2-methyl-4H-imidazo[1,2-a][1,4]benzodiazepine-5-oxide;
8-cyano-6-(2-fluorophenyl)-2-methyl-4H-imidazo[1,2-a][1,4]benzodiazepine-5-oxide;
8-methylthio-6-(2-fluorophenyl)-2-methyl-4H-imidazo[1,2-a][1,4]benzodiazepine-5-oxide;
8-chloro-6-(2-pyrimidyl)-2-methyl-4H-imidazo[1,2-a][1,4]benzodiazepine-5-oxide;
8-bromo-6-(2-furyl)-2-methyl-4H-imidazo[1,2-a][1,4]benzodiazepine-5-oxide;
8-fluoro-6-(2-pyrryl)-2-methyl-4H-imidazo[1,2-a][1,4]benzodiazepine-5-oxide;
8-nitro-6-(2-thienyl)-2-methyl-4H-imidazo[1,2-a][1,4]benzodiazepine-5-oxide;
8-trifluoromethyl-6-cyclohexyl-2-methyl-4H-imidazo[1,2-a][1,4]benzodiazepine-5-oxide;
8-cyano-6-(1-cyclohexenyl)-2-methyl-4H-imidazo[1,2-a][1,4]benzodiazepine-5-oxide; and
8-methylthio-2,6-dimethyl-4H-imidazo[1,2-a][1,4]benzodiazepine-5-oxide, respectively.

EXAMPLE 29

8-chloro-4-hydroxy-1-methyl-6-phenyl-4H-imidazo[1,2-a][1,4]benzodiazepine acetate (1b)

A stirred mixture of 1.0 g of 8-chloro-1-methyl-6-phenyl-4H-imidazo[1,2-a][1,4]benzodiazepine-5-oxide (III), 5 ml. of acetic anhydride and 3 ml. of acetic acid is warmed on the steam bath, under nitrogen, for 30 minutes and concentrated in vacuo. The residue is suspended in water, neutralized with sodium carbonate and extracted with methylene chloride. The extract is dried, concentrated and chromatographed on silica gel eluting with ethyl acetate to yield 8-chloro-4-hydroxy-1-methyl-6-phenyl-4H-imidazo[1,2-a][1,4]benzodiazepine acetate.

EXAMPLE 30

8-chloro-6-(2-chlorophenyl)-4-hydroxy-1-methyl-4H-imidazo[1,2-a][1,4]benzodiazepine acetate (1b)

A stirred mixture of 1.0 g. of 8-chloro-6-(2-chlorophenyl)-1-methyl-4H-imidazo[1,2-a][1,4]benzodiazepine-5-oxide (III), 5 ml. of acetic anhydride and 3 ml. of acetic acid is warmed on the steam bath, under nitrogen, for 30 minutes and concentrated in vacuo. The residue is suspended in water, neutralized with sodium carbonate and extracted with methylene chloride. The extract is dried, concentrated and chromatographed on silica gel eluting with ethyl acetate to yield 8-chloro-6-(2-chlorophenyl)-4-hydroxy-1-methyl-4H-imidazo[1,2-a][1,4]benzodiazepine acetate.

In the same manner, following the procedure of Examples 29 and 30, above, the other 4H-imidazo[1,2-a]8 1,4]benzodiazepine-5-oxides of formula III can likewise be converted to the 4-acyloxy derivatives giving the corresponding compounds of formula 1b. The following are representative:
8-chloro-6-(2,6-difluorophenyl)-1-ethyl-4H-imidazo[1,2-a][1,4]benzodiazepine-5-oxide to obtain 8-chloro-4-hydroxy-6-(2,6-difluorophenyl)-1-ethyl-4H-imidazo[1,2-a][1,4]benzodiazepine acetate;
8-trifluoromethyl-6-phenyl-1-propyl-4H-imidazo[1,2-a][1,4]benzodiazepine-5-oxide to obtain 8-trifluoromethyl-4-hydroxy-6-phenyl-1-propyl-4H-imidazo[1,2-a][1,4]benzodiazepine acetate;
8-bromo-1-methyl-6-(2-pyridyl)-4H-imidazo[1,2-a][1,4]benzodiazepine-5-oxide to obtain 8-bromo-4-hydroxy-1-methyl-6-(2-pyridyl)-4H-imidazo[1,2-a][1,4]benzodiazepine acetate;
8-chloro-2,6-dimethyl-1-propyl-4H-imidazo[1,2-a][1,4]benzodiazepine-5-oxide to obtain 8-chloro-2,6-dimethyl-4-hydroxy-1-propyl-4-H-imidazo[1,2-a][1,4]benzodiazepine acetate;
8-chloro-1,2,4-trimethyl-6-phenyl-4H-imidazo[1,2-a][1,4]benzodiazepine-5-oxide to obtain 8-chloro-4-hydroxy-1,2,4-trimethyl-6-phenyl-4H-imidazo[1,2-a][1,4]benzodiazepine acetate;
8-chloro-1,2-dimethyl-6-(2-chlorophenyl)-4H-imidazo-[1,2-a][1,4]benzodiazepine-5-oxide to obtain 8-chloro-4-hydroxy-1,2-dimethyl-6-(2-chlorophenyl)-4H-imidazo[1,2-a]-[1,4]benzodiazepine acetate;
8-chloro-6-phenyl-4H-imidazo[1,2-a][1,4]benzodiazepine-5-oxide to obtain 8-chloro-4-hydroxy-6-phenyl-4H-imidazo-[1,2-a][1,4]benzodiazepine acetate;
8-chloro-6-(2-chlorophenyl)-4H-imidazo[1,2-a][1,4]benzodiazepine-5-oxide to obtain 8-chloro-4-hydroxy-6-(2-chlorophenyl)-4H-imidazo[1,2-a][1,4]benzodiazepine acetate;
8-chloro-6-(2-pyridyl)-4H-imidazo[1,2-a][1,4]benzodiazepine-5-oxide to obtain 8-chloro-4-hydroxy-6-(2-pyridyl)-4H-imidazo[1,2-a][1,4]benzodiazepine acetate;
8-chloro-2,4-dimethyl-6-phenyl-4H-imidazo[1,2-a][1,4]benzodiazepine-5-oxide to obtain 8-chloro-2,4-dimethyl-4-hydroxy-6-phenyl-4H-imidazo[1,2-a][1,4]benzodiazepine acetate; and
8-chloro-6-(2-chlorophenyl)-2-methyl-4H-imidazo[1,2-a][1,4]benzodiazepine-5-oxide to obtain 8-chloro-6-(2-chlorophenyl)-4-hydroxy-2-methyl-4H-imidazo[1,2-a][1,4]benzodiazepine acetate.

Similarly, following the procedure of Examples 29 and 30, the other 5-oxides of formula III can likewsie be converted to the corresponding 4-acetates, for example the compounds listed in Example 28, above, give:
8-bromo-4-hydroxy-6-phenyl-1-methyl-4H-imidazo[1,2-a][1,4]benzodiazepine acetate;
8-fluoro-4-hydroxy-6-phenyl-1-methyl-4H-imidazo[1,2-a][1,4]benzodiazepine acetate;
8-nitro-4-hydroxy-6-phenyl-1-methyl-4H-imidazo[1,2-a][1,4]benzodiazepine acetate;
8-trifluoromethyl-4-hydroxy-6-phenyl-1-methyl-4H-imidazo[1,2-a][1,4]benzodiazepine acetate;
8-cyano-4-hydroxy-6-phenyl-1-methyl-4H-imidazo[1,2-a][1,4]benzodiazepine acetate;
8-methylthio-4-hydroxy-6-phenyl-1-methyl-4H-imidazo-[1,2-a][1,4]benzodiazepine acetate;
8-bromo-4-hydroxy-6-(2-chlorophenyl)-1-methyl-4H-imidazo[1,2-a][1,4]benzodiazepine acetate;
8-fluoro-4-hydroxy-6-(2-chlorophenyl)-1-methyl-4H-imidazo[1,2-a][1,4]benzodiazepine acetate;
8-nitro-4-hydroxy-6-(2-chlorophenyl)-1-methyl-4H-imidazo[1,2-a][1,4]benzodiazepine acetate;
8-trifluoromethyl-4-hydroxy-6-(2-chlorophenyl)-1-methyl-4H-imidazo[1,2-a][1,4]benzodiazepine acetate;
8-cyano-4-hydroxy-6-(2-chlorophenyl)-1-methyl-4H-imidazo[1,2-a][1,4]benzodiazepine acetate;
8-methylthio-4-hydroxy-6-(2-chlorophenyl)-1-methyl-4H-imidazo[1,2-a][1,4]benzodiazepine acetate;
8-chloro-4-hydroxy-6-(2-fluorophenyl)-1-methyl-4H-imidazo[1,2-a][1,4]benzodiazepine acetate;
8-bromo-4-hydroxy-6-(2-fluorophenyl)-1-methyl-4H-imidazo[1,2-a][1,4]benzodiazepine acetate;

8-fluoro-4-hydroxy-6-(2-fluorophenyl)-1-methyl-4H-imidazo[1,2-a][1,4]benzodiazepine acetate;
8-nitro-4-hydroxy-6-(2-fluorophenyl)-1-methyl-4H-imidazo[1,2-a][1,4]benzodiazepine acetate;
8-trifluoromethyl-4-hydroxy-6-(2-fluorophenyl)-1-methyl-4H-imidazo[1,2-a][1,4]benzodiazepine acetate;
8-cyano-4-hydroxy-6-(2-fluorophenyl)-1-methyl-4H-imidazo[1,2-a][1,4]benzodiazepine acetate;
8-methylthio-4-hydroxy-6-(2-fluorophenyl)-1-methyl-4H-imidazo[1,2-a][1,4]benzodiazepine acetate;
8-chloro-4-hydroxy-6-(2-pyrimidyl)-1-methyl-4H-imidazo[1,2-a][1,4]benzodiazepine acetate;
8-bromo-4-hydroxy-6-(2-furyl)-1-methyl-4H-imidazo[1,2-a][1,4]benzodiazepine acetate;
8-fluoro-4-hydroxy-6-(2-pyrryl)-1-methyl-4H-imidazo[1,2-a][1,4]benzodiazepine acetate;
8-nitro-4-hydroxy-6-(2-thienyl)-1-methyl-4H-imidazo[1,2-a][1,4]benzodiazepine acetate;
8-trifluoromethyl-4-hydroxy-6-cyclohexyl-1-methyl-4H-imidazo[1,2-a][1,4]benzodiazepine acetate;
8-cyano-4-hydroxy-6-(1-cyclohexenyl)-1-methyl-4H-imidazo[1,2-a][1,4]benzodiazepine acetate;
8-methylthio-4-hydroxy-1,6-dimethyl-4H-imidazo[1,2-a][1,4]benzodiazepine acetate;
8-bromo-4-hydroxy-6-phenyl-1,2-dimethyl-4H-imidazo[1,2-a][1,4]benzodiazepine acetate;
8-fluoro-4-hydroxy-6-phenyl-1,2-dimethyl-4H-imidazo[1,2-a][1,4]benzodiazepine acetate;
8-nitro-4-hydroxy-6-phenyl-1,2-dimethyl-4H-imidazo[1,2-a][1,4]benzodiazepine acetate;
8-trifluoromethyl-4-hydroxy-6-phenyl-1,2-dimethyl-4H-imidazo[1,2-a][1,4]benzodiazepine acetate;
8-cyano-4-hydroxy-6-phenyl-1,2-dimethyl-4H-imidazo[1,2-a][1,4]benzodiazepine acetate;
8-methylthio-4-hydroxy-6-phenyl-1,2-dimethyl-4H-imidazo[1,2-a][1,4]benzodiazepine acetate;
8-bromo-4-hydroxy-6-(2-chlorophenyl)-1,2-dimethyl-4H-imidazo[1,2-a][1,4]benzodiazepine acetate;
8-fluoro-4-hydroxy-6-(2-chlorophenyl)-1,2-dimethyl-4H-imidazo[1,2-a][1,4]benzodiazepine acetate;
8-nitro-4-hydroxy-6-(2-chlorophenyl)-1,2-dimethyl-4H-imidazo[1,2-a][1,4]benzodiazepine acetate;
8-trifluoromethyl-4-hydroxy-6-(2-chlorophenyl)-1,2-dimethyl-4H-imidazo[1,2-a][1,4]benzodiazepine acetate;
8-cyano-4-hydroxy-6-(2-chlorophenyl)-1,2-dimethyl-4H-imidazo[1,2-a][1,4]benzodiazepine acetate;
8-methylthio-4-hydroxy-6-(2-chlorophenyl)-1,2-dimethyl-4H-imidazo[1,2-a][1,4]benzodiazepine acetate;
8-chloro-4-hydroxy-6-(2-fluorophenyl)-1,2-dimethyl-4H-imidazo[1,2-a][1,4]benzodiazepine acetate;
8-bromo-4-hydroxy-6-(2-fluorophenyl)-1,2-dimethyl-4H-imidazo[1,2-a][1,4]benzodiazepine acetate;
8-fluoro-4-hydroxy-6-(2-fluorophenyl)-1,2-dimethyl-4H-imidazo[1,2-a][1,4]benzodiazepine acetate;
8-nitro-4-hydroxy-6-(2-fluorophenyl)-1,2-dimethyl-4H-imidazo[1,2-a][1,4]benzodiazepine acetate;
8-trifluoromethyl-4-hydroxy-6-(2-fluorophenyl)-1,2-dimethyl-4H-imidazo[1,2-a][1,4]benzodiazepine acetate;
8-cyano-4-hydroxy-6-(2-fluorophenyl)-1,2-dimethyl-4H-imidazo[1,2-a][1,4]benzodiazepine acetate;
8-methylthio-4-hydroxy-6-(2-fluorophenyl)-1,2-dimethyl-4H-imidazo[1,2-a][1,4]benzodiazepine acetate;
8-chloro-4-hydroxy-6-(2-pyrimidyl)-1,2-dimethyl-4H-imidazo[1,2-a][1,4]benzodiazepine acetate;
8-bromo-4-hydroxy-6-(2-furyl)-1,2-dimethyl-4H-imidazo-[1,2-a][1,4]benzodiazepine acetate;
8-fluoro-4-hydroxy-6-(2-pyrryl)-1,2-dimethyl-4H-imidazo[1,2-a][1,4]benzodiazepine acetate;
8-nitro-4-hydroxy-6-(2-thienyl)-1,2-dimethyl-4H-imidazo[1,2-a][1,4]benzodiazepine acetate;
8-trifluoromethyl-4-hydroxy-6-cyclohexyl-1,2-dimethyl-4H-imidazo[1,2-a][1,4]benzodiazepine acetate;
8-cyano-4-hydroxy-6-(1-cyclohexenyl)-1,2-dimethyl-4H-imidazo[1,2-a][1,4]benzodiazepine acetate;
8-methylthio-4-hydroxy-1,2,6-trimethyl-4H-imidazo[1,2-a][1,4]benzodiazepine acetate;
8-bromo-4-hydroxy-6-phenyl-4H-imidazo[1,2-a][1,4]benzodiazepine acetate;
8-fluoro-4-hydroxy-6-phenyl-4H-imidazo[1,2-a][1,4]benzodiazepine acetate;
8-nitro-4-hydroxy-6-phenyl-4H-imidazo[1,2-a][1,4]benzodiazepine acetate;
8-trifluoromethyl-4-hydroxy-6-phenyl-4H-imidazo[1,2-a][1,4]benzodiazepine acetate;
8-cyano-4-hydroxy-6-phenyl-4H-imidazo[1,2-a][1,4]benzodiazepine acetate;
8-methylthio-4-hydroxy-6-phenyl-4H-imidazo[1,2-a][1,4]benzodiazepine acetate;
8-bromo-4-hydroxy-6-(2-chlorophenyl)-4H-imidazo[1,2-a][1,4]benzodiazepine acetate;
8-fluoro-4-hydroxy-6-(2-chlorophenyl)-4H-imidazo[1,2-a][1,4]benzodiazepine acetate;
8-nitro-4-hydroxy-6-(2-chlorophenyl)-4H-imidazo[1,2-a][1,4]benzodiazepine acetate;
8-trifluoromethyl-4-hydroxy-6-(2-chlorophenyl)-4H-imidazo[1,2-a][1,4]benzodiazepine acetate;
8-cyano-4-hydroxy-6-(2-chlorophenyl)-4H-imidazo[1,2-a][1,4]benzodiazepine acetate;
8-methylthio-4-hydroxy-6-(2-chlorophenyl)-4H-imidazo[1,2-a][1,4]benzodiazepine acetate;
8-chloro-4-hydroxy-6-(2-fluorophenyl)-4H-imidazo[1,2-a][1,4]benzodiazepine acetate;
8-bromo-4-hydroxy-6-(2-fluorophenyl)-4H-imidazo[1,2-a][1,4]benzodiazepine acetate;
8-fluoro-4-hydroxy-6-(2-fluorophenyl)-2H-imidazo[1,2-a][1,4]benzodiazepine acetate;
8-nitro-4-hydroxy-6-(2-fluorophenyl)-4H-imidazo[1,2-a][1,4]benzodiazepine acetate;
8-trifluoromethyl-4-hydroxy-6-(2-fluorophenyl)-4H-imidazo[1,2-a][1,4]benzodiazepine acetate;
8-cyano-4-hydroxy-6-(2-fluorophenyl)-4H-imidazo[1,2-a][1,4]benzodiazepine acetate;
8-methylthio-4-hydroxy-6-(2-fluorophenyl)-4H-imidazo[1,2-a][1,4]benzodiazepine acetate;
8-chloro-4-hydroxy-6-(2-pyrimidyl)-4H-imidazo[1,2-a][1,4]benzodiazepine acetate;
8-bromo-4-hydroxy-6-(2-furyl)-4H-imidazo[1,2-a][1,4]benzodiazepine acetate;
8-fluoro-4-hydroxy-6-(2-pyrryl)-4H-imidazo[1,2-a][1,4]benzodiazepine acetate;
8-nitro-4-hydroxy-6-(2-thienyl)-4H-imidazo[1,2-a][1,4]benzodiazepine acetate;
8-trifluoromethyl-4-hydroxy-6-cyclohexyl-4H-imidazo[1,2-a][1,4]benzodiazepine acetate;
8-cyano-4-hydroxy-6-(1-cyclohexenyl)-4H-imidazo[1,2-a][1,4]benzodiazepine acetate;
8-methylthio-4-hydroxy-6-methyl-4H-imidazo[1,2-a][1,4]benzodiazepine acetate;
8-bromo-4-hydroxy-6-phenyl-2-methyl-4H-imidazo[1,2-a][1,4]benzodiazepine acetate;

8-fluoro-4-hydroxy-6-phenyl-2-methyl-4H-imidazo[1,2-a][1,4]benzodiazepine acetate;
8-nitro-4-hydroxy-6-phenyl-2-methyl-4H-imidazo[1,2-a][1,4]benzodiazepine acetate;
8-trifluoromethyl-4-hydroxy-6-phenyl-2-methyl-4H-imidazo[1,2-a][1,4]benzodiazepine acetate;
8-cyano-4-hydroxy-6-phenyl-2-methyl-4H-imidazo[1,2-a][1,4]benzodiazepine acetate;
8-methylthio-4-hydroxy-6-phenyl-2-methyl-4H-imidazo[1,2-a][1,4]benzodiazepine acetate;
8-bromo-4-hydroxy-6-(2-chlorophenyl)-2-methyl-4H-imidazo[1,2-a][1,4]benzodiazepine acetate;
8-fluoro-4-hydroxy-6-(2-chlorophenyl)-2-methyl-4H-imidazo[1,2-a][1,4]benzodiazepine acetate;
8-nitro-4-hydroxy-6-(2-chlorophenyl)-2-methyl-4H-imidazo[1,2-a][1,4]benzodiazepine acetate;
8-trifluoromethyl-4-hydroxy-6-(2-chlorophenyl)-2-methyl-4H-imidazo[1,2-a][1,4]benzodiazepine acetate;
8-cyano-4-hydroxy-6-(2-chlorophenyl)-2-methyl-4H-imidazo[1,2-a][1,4]benzodiazepine acetate;
8-methylthio-4-hydroxy-6-(2-chlorophenyl)-2-methyl-4H-imidazo[1,2-a][1,4]benzodiazepine acetate;
8-chloro-4-hydroxy-6-(2-fluorophenyl)-2-methyl-4H-imidazo[1,2-a][1,4]benzodiazepine acetate;
8-bromo-4-hydroxy-6-(2-fluorophenyl)-2-methyl-4H-imidazo[1,2-a][1,4]benzodiazepine acetate;
8-fluoro-4-hydroxy-6-(2-fluorophenyl)-2-methyl-4H-imidazo[1,2-a][1,4]benzodiazepine acetate;
8-nitro-4-hydroxy-6-(2-fluorophenyl)-2-methyl-4H-imidazo[1,2-a][1,4]benzodiazepine acetate;
8-trifluoromethyl-4-hydroxy-6-(2-fluorophenyl)-2-methyl-4H-imidazo[1,2-a][1,4]benzodiazepine acetate;
8-cyano-4-hydroxy-6-(2-fluorophenyl)-2-methyl-4H-imidazo[1,2-a][1,4]benzodiazepine acetate;
8-methylthio-4-hydroxy-6-(2-fluorophenyl)-2-methyl-4H-imidazo[1,2-a][1,4]benzodiazepine acetate;
8-chloro-4-hydroxy-6-(2-pyrimidyl)-2-methyl-4H-imidazo[1,2-a][1,4]benzodiazepine acetate;
8-bromo-4-hydroxy-6-(2-furyl)-2-methyl-4H-imidazo[1,2-a][1,4]benzodiazepine acetate;
8-fluoro-4-hydroxy-6-(2-pyrryl)-2-methyl-4H-imidazo[1,2-a][1,4]benzodiazepine acetate;
8-nitro-4-hydroxy-6-(2-thienyl)-2-methyl-4H-imidazo[1,2-a][1,4]benzodiazepine acetate;
8-trifluoromethyl-4-hydroxy-6-cyclohexyl-2-methyl-4H-imidazo[1,2-a][1,4]benzodiazepine acetate;
8-cyano-4-hydroxy-6-(1-cyclohexenyl)-2-methyl-4H-imidazo[1,2-a][1,4]benzodiazepine acetate; and
8-methylthio-4-hydroxy-2,6-dimethyl-4H-imidazo[1,2-a][1,4]benzodiazepine acetate; respectively.

Following the procedures of Examples 29 and 20, above, but substituting propionic anhydride and propionic acid in place of acetic anhydride and acetic acid gives the corresponding propionates of formula 1b, for example the propionates corresponding to the acetates listed.

EXAMPLE 31

8-chloro-4-hydroxy-1-methyl-6-phenyl-4H-imidazo[1,2-a][1,4]benzodiazepine (1c)

A stirred suspension of 294 mg. of 8-chloro-4-hydroxy-1-methyl-6-phenyl-4H-imidazo[1,2-a][1,4]benzodiazepine acetate (1b) in 25 ml. of absolute ethanol under nitrogen is stirred for about 3 hours at room temperature (about 25° C.) with 2.2 ml. of 0.5N aqueous sodium hydroxide, poured into water and extracted with methylene chloride. The extract was dried and concentrated and the residue chromatographed on silica gel, eluting with ethyl acetate to yield 8-chloro-4-hydroxy-1-methyl-6-phenyl-4H-imidazo[1,2-a][1,4]benzodiazepine.

In the same manner following the procedure of Example 31, above, other acetates of formula 1b can likewise be hydrolyzed to obtain the corresponding free alcohols of formula 1c. The following are representative.

8-chloro-6-(2-chlorophenyl)-4-hydroxy-1-methyl-4H-imidazo[1,2-a][1,4]benzodiazepine acetate to obtain 8-chloro-6-(2-chlorophenyl)-4-hydroxy-1-methyl-4H-imidazo[1,2-a][1,4]benzodiazepine;
8-chloro-4-hydroxy-6-(2,6-difluorophenyl)-1-ethyl-4H-imidazo[1,2-a][1,4]benzodiazepine acetate to obtain 8-chloro-4-hydroxy-6-(2,6-difluorophenyl)-1-ethyl-4H-imidazo[1,2-a][1,4]benzodiazepine;
8-trifluoromethyl-4-hydroxy-6-phenyl-1-propyl-4H-imidazo[1,2-a][1,4]benzodiazepine acetate to obtain 8-trifluoromethyl-4-hydroxy-6-phenyl-1-propyl-4H-imidazo[1,2-a][1,4]benzodiazepine;
8-bromo-4-hydroxy-1-methyl-6-(2-pyridyl)-4H-imidazo-[1,2-a][1,4]benzodiazepine acetate to obtain 8-bromo-4-hydroxy-1-methyl-6-(2-pyridyl)-4H-imidazo[1,2-a][1,4]benzodiazepine;
8-chloro-2,6-dimethyl-4-hydroxy-1-propyl-4H-imidazo-[1,2-a][1,4]benzodiazepine acetate to obtain 8-chloro-2,6-dimethyl-4-hydroxy-1-propyl-4H-imidazo[1,2-a][1,4]benzodiazepine; 8-chloro-4-hydroxy-1,2,4-trimethyl-6-phenyl-4H-imidazo[1,2-a][1,4]benzodiazepine acetate to obtain 8-chloro-4-hydroxy-1,2,4-trimethyl-6-phenyl-4H-imidazo[1,2-a][1,4]benzodiazepine;
8-chloro-4-hydroxy-1,2-dimethyl-6-(2-chlorophenyl)-4H-imidazo[1,2-a][1,4]benzodiazepine acetate to obtain 8-chloro-4-hydroxy-1,2-dimethyl-6-(2-chlorophenyl)-4H-imidazo[1,2-a][1,4]benzodiazepine;
8-chloro-4-hydroxy-6-phenyl-4H-imidazo[1,2-a][1,4]benzodiazepine acetate to obtain 8-chloro-4-hydroxy-6-phenyl-4H-imidazo[1,2-a][1,4]benzodiazepine;
8-chloro-4-hydroxy-6-(2-chlorophenyl)-4H-imidazo[1,2-a][1,4]benzodiazepine acetate to obtain 8-chloro-4-hydroxy-6-(2-chlorophenyl)-4H-imidazo[1,2-a][1,4]benzodiazepine;
8-chloro-4-hydroxy-6-(2-pyridyl)-4H-imidazo[1,2-a][1,4]benzodiazepine acetate to obtain 8-chloro-4-hydroxy-6-(2-pyridyl)-4H-imidazo[1,2-a][1,4]benzodiazepine;
8-chloro-2,4-dimethyl-4-hydroxy-6-phenyl-4H-imidazo[1,2-a][1,4]benzodiazepine acetate to obtain 8-chloro-2,4-dimethyl-4-hydroxy-6-phenyl-4H-imidazo[1,2-a][1,4]benzodiazepine; and
8-chloro-6-(2-chlorophenyl)-4-hydroxy-2-methyl-4H-imidazo[1,2-a][1,4]benzodiazepine acetate to obtain 8-chloro-6-(2-chlorophenyl)-4-hydroxy-2-methyl-4H-imidazo[1,2-a][1,4]benzodiazepine.

Similarly, following the procedure of Example 31, the other acetates of formula 1b can likewise be hydrolyzed to obtain the corresponding free alcohols of formula 1c. For example the acetates listed in Example 30, above.

Similarly, following the procedure of Example 31, the corresponding propionate esters of formula 1b can likewise be hydrolyzed to obtain the corresponding free alcohols of formula 1c.

We claim:
1. A compound of the formula:

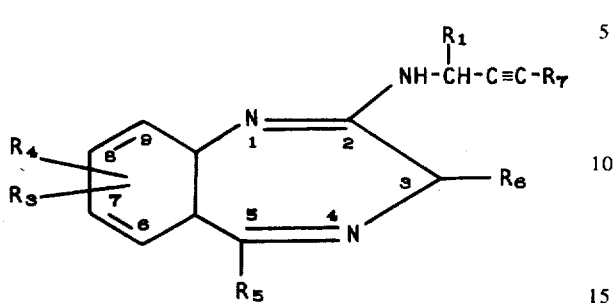

wherein $R_1$ and $R_6$ are each selected from the group consisting of hydrogen and alkyl of 1 to 3 carbon atoms, inclusive; $R_3$ and $R_4$ are each selected from the group consisting of hydrogen, halogen, nitro, trifluoromethyl, alkylthio in which the carbon chain moieties are of 1 to 3 carbon atoms, inclusive; $R_5$ is selected from the group consisting of pyridyl and a phenyl radical of the formula

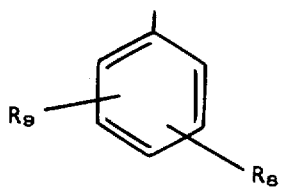

in which $R_8$ and $R_9$ each have the same meaning as given above for $R_3$ and $R_4$; and $R_7$ is selected from the group consisting of hydrogen, methyl and ethyl.

2. 7-chloro-6-phenyl-2-(2-propynylamino)-3H-1,4-benzodiazepine, the compound of claim 1, wherein $R_1$, $R_4$, $R_6$ and $R_7$ are each hydrogen; $R_3$ is 7-chloro; and $R_5$ is phenyl.

3. 7-chloro-5-(2-chlorophenyl)-2-(2-propynylamino)-3H-1,4-benzodiazepine, the compound of claim 1, wherein $R_1$, $R_4$, $R_6$ and $R_7$ are each hydrogen, $R_3$ is 7-chloro; and $R_5$ is 2-chlorophenyl.

* * * * *